United States Patent
Hoshino et al.

(10) Patent No.: US 10,696,848 B2
(45) Date of Patent: Jun. 30, 2020

(54) FLUORINATED ETHER COMPOUND, COATING LIQUID, ARTICLE AND NOVEL COMPOUNDS

(71) Applicant: AGC Inc., Chiyoda-ku (JP)

(72) Inventors: Taiki Hoshino, Chiyoda-ku (JP); Kazue Toda, Chiyoda-ku (JP); Eiichiro Anraku, Chiyoda-ku (JP); Masahiro Itoh, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/152,450

(22) Filed: Oct. 5, 2018

(65) Prior Publication Data

US 2019/0040266 A1    Feb. 7, 2019

Related U.S. Application Data

(63) Continuation of application No. PCT/JP2017/007897, filed on Feb. 28, 2017.

(30) Foreign Application Priority Data

Apr. 25, 2016 (JP) .................. 2016-087043
Aug. 15, 2016 (JP) .................. 2016-159202

(51) Int. Cl.
```
C09D 5/00      (2006.01)
C07C 211/22    (2006.01)
C09D 171/00    (2006.01)
C08G 65/336    (2006.01)
C23C 14/24     (2006.01)
C07C 255/06    (2006.01)
C08G 65/00     (2006.01)
C08G 65/323    (2006.01)
C07C 255/07    (2006.01)
C07F 7/18      (2006.01)
B05D 1/00      (2006.01)
B05D 5/08      (2006.01)
B05D 1/02      (2006.01)
C23C 14/12     (2006.01)
```
(52) U.S. Cl.
CPC ............. *C09D 5/00* (2013.01); *C07C 211/22* (2013.01); *C07C 255/06* (2013.01); *C07C 255/07* (2013.01); *C07F 7/1804* (2013.01); *C08G 65/007* (2013.01); *C08G 65/323* (2013.01); *C08G 65/336* (2013.01); *C09D 171/00* (2013.01); *C23C 14/24* (2013.01); *B05D 1/02* (2013.01); *B05D 1/60* (2013.01); *B05D 5/083* (2013.01); *C23C 14/12* (2013.01)

(58) Field of Classification Search
None
See application file for complete search history.

(56) References Cited

U.S. PATENT DOCUMENTS

| | | | |
|---|---|---|---|
| 6,277,485 B1* | 8/2001 | Invie | C09D 183/12 |
| | | | 428/336 |
| 2010/0272910 A1* | 10/2010 | Kishita | C09D 5/165 |
| | | | 427/387 |
| 2012/0077041 A1 | 3/2012 | Yamane et al. | |

FOREIGN PATENT DOCUMENTS

| | | |
|---|---|---|
| JP | 2012-072272 | 4/2012 |
| JP | 2014-070163 | 4/2014 |
| JP | 2014-144935 | 8/2014 |
| JP | 2015-168785 | 9/2015 |
| WO | WO 2009/008380 A1 | 1/2009 |
| WO | WO 2013/121984 A1 | 8/2013 |
| WO | WO 2015/087902 A1 | 6/2015 |
| WO | WO 2017/038830 A1 | 3/2017 |

OTHER PUBLICATIONS

International Search Report dated Jun. 6, 2017 in PCT/JP2017/007897 filed Feb. 28, 2017 (with English Translation).
Nicolas Galy, et al., "Allylsilane and diallylsilane reactions with functionalized ethylene ketals or benzodioxoles," Tetrahedron 67, 2011, pp. 1448-1455.

* cited by examiner

*Primary Examiner* — Clinton A Brooks
*Assistant Examiner* — Kofi Adzamli
(74) *Attorney, Agent, or Firm* — Oblon, McClelland, Maier & Neustadt, L.L.P.

(57) ABSTRACT

The present invention provides: a fluorinated ether compound and a coating liquid capable of forming a surface layer excellent in water/oil repellency, abrasion resistance, fingerprint stain removability and lubricity and an article having a surface layer excellent in water/oil repellency, abrasion resistance, fingerprint stain removability and lubricity. Provided is a fluorinated ether compound represented by $[R^f\text{-}G\text{-}]_a Z[\text{---}(O\text{---}R^2)_c\text{---}SiR^3{}_n L_{3-n}]_b$ wherein $R^f$: a linear polyfluoroalkyl group having at least two carbon atoms, which has at least one etheric oxygen between carbon-carbon atoms, G: $\text{---}R^1\text{---}O\text{---}$, $\text{---}R^1\text{---}CONH\text{---}$, $\text{---}CONH\text{---}$ or a single bond, $R^1$: an alkylene group, Z: a hydrocarbon group having a valence of (a+b) or the like, $R^2$: an alkylene group, $R^3$: a monovalent hydrocarbon group or the like, L: a hydrolyzable group, n: from 0 to 2, a: an integer of at least 1, b: an integer of at least 1, (a+b): at least 3, when a is 1, b is at least 4, and when a is at least 2, b is at least 1, and c: 0 or 1.

13 Claims, No Drawings

FLUORINATED ETHER COMPOUND, COATING LIQUID, ARTICLE AND NOVEL COMPOUNDS

TECHNICAL FIELD

The present invention relates to a fluorinated compound, a coating liquid, an article and novel compounds.

BACKGROUND ART

Fluorinated compounds show high lubricity, water/oil repellency, etc. and are thus useful for surface treating agents. Such surface treating agents impart water/oil repellency to a substrate surface, thereby making it easy to wipe off stains from the substrate surface with improved stain removability. Among such fluorinated compounds, a fluorinated ether compound having a poly(oxy perfluoroalkylene) chain, wherein an ether bond (—O—) is present in the perfluoroalkylene chain, is particularly excellent in the fat and oil stain removability.

Surface treating agents containing such a fluorinated ether compound are useful in applications which require long-lasting water/oil repellency that withstands repeated rubs by fingers (abrasion resistance) and long-lasting ease of removal of fingerprints from a surface by wiping (fingerprint stain removability), e.g. as a surface treating agent for a member constituting a surface to be touched by a finger, of a touch panel.

Introduction of a hydrolyzable silyl group to the end of a fluorinated ether compound imparts abrasion resistance to a surface layer formed on a substrate through formation of chemical bonds between the fluorinated ether compound and the substrate. A fluorinated ether compound having three hydrolyzable silyl groups at both ends via a branched structure of pentaerythritol was proposed with the aim of forming a surface layer with excellent abrasion resistance (Patent Document 1).

PRIOR ART DOCUMENTS

Patent Documents

Patent Document 1: JP-A-2014-070163

DISCLOSURE OF INVENTION

Technical Problem

However, according to the findings by the present inventor, the fluorinated ether compound disclosed in Patent Document 1 has the following problems.

The resulting surface layer lacks sufficient lubricity (smooth touch on fingers) and abrasion resistance because the hydrolyzable silyl groups at both ends react with the substrate or intermolecularly to fix both ends of the fluorinated ether compound.

The resulting surface layer lacks sufficient abrasion resistance and lubricity because of the branched poly(oxyperfluoroalkylene) chain.

It is an object of the present invention to provide a fluorinated ether compound and coating liquid capable of forming a surface layer excellent in water/oil repellency, abrasion resistance, fingerprint stain removability and lubricity, an article having a surface layer excellent in water/oil repellency, abrasion resistance, fingerprint stain removability and lubricity, and a novel compound useful as an intermediate for producing the fluorinated ether compound.

Solution to Problem

The present invention provides a fluorinated ether composition, a method for its production, a coating liquid, an article and a novel compound, having the following constructions [1] to [14].

[1] A fluorinated ether compound represented by the following formula (1):

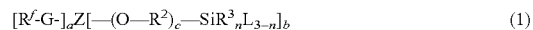

$$[R^f\text{-}G\text{-}]_a Z[-(O-R^2)_c-SiR^3{}_n L_{3-n}]_b \quad (1)$$

wherein $R^f$ is a linear polyfluoroalkyl group having at least two carbon atoms, which has at least one etheric oxygen between carbon-carbon atoms and has at least one fluorine atoms on a carbon atom bonded to G or Z, G is —$R^1$—O—, —$R^1$—CONH—, —CONH— or a single bond, $R^1$ is an alkylene group. Z is a hydrocarbon group having a valence of (a+b) or a hydrocarbon group having at least two carbon atoms, having at least one etheric oxygen atom between carbon-carbon atoms and having a valence of (a+b), $R^2$ is an alkylene group, $R^3$ is a hydrogen atom or a monovalent hydrocarbon group, L is a hydrolyzable group, n is an integer of from 0 to 2, a is an integer of at least 1, b is an integer of at least 1, (a+b) is at least 3, when a is 1, b is at least 4, and when a is at least 2, b is at least 1, provided that when a is at least 2, each [$R^f$-G-] may be identical with or different from one another, and when b is at least 2, each [—(O—$R^2$)$_c$-SiR$^3{}_n$L$_{3-n}$] may be identical with or different from one another, and c is 0 or 1.

[2] The fluorinated ether compound according to [1], wherein $R^2$ is a $C_{4-14}$ alkylene group.

[3] The fluorinated ether compound according to [1] or [2], wherein Z is a group represented by the following formula (Z-1), a group represented by the following formula (Z-2), a group represented by the following formula (Z-3), a group represented by the following formula (Z-4) or a group represented by the following formula (Z-5):

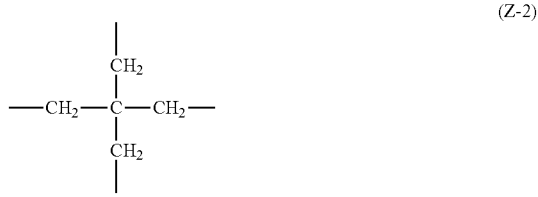

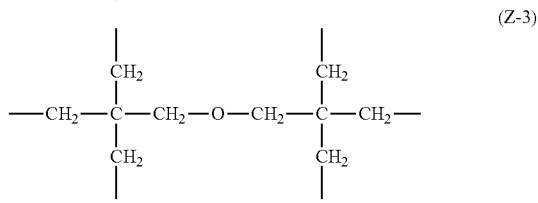

-continued

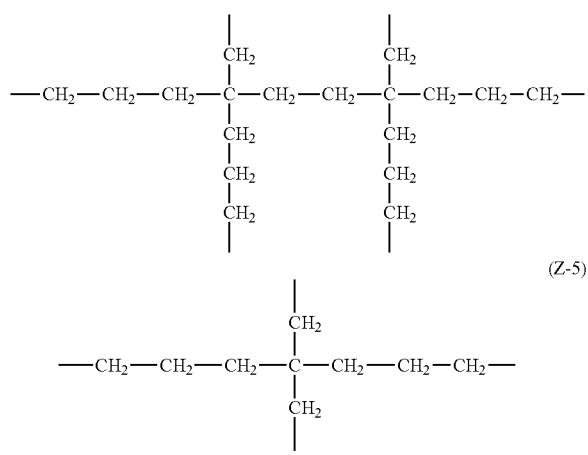

(Z-4)

(Z-5)

wherein $R^4$ is an alkyl group.

[4] The fluorinated ether compound according to any one of [1] to [3], wherein $R^1$ is —$CH_2$—.

[5] The fluorinated ether compound according to any one of [1] to [4], wherein $R^f$ is a group represented by the following formula ($R^f$-0):

$$R^{f1}O(R^{f2}O)_{m1}(R^{f3}O)_{m2}R^{f4}— \qquad (R^f\text{-}0)$$

wherein when m1 is 0, $R^{f1}$ is a $C_{1-20}$ linear perfluoroalkyl group, and when m1 is at least 1, $R^{f1}$ is a $C_{1-20}$ linear perfluoroalkyl group or a $C_{2-20}$ linear perfluoroalkyl group having at least one etheric oxygen atom between carbon-carbon atoms, $R^{f2}$ is a $C_{1-10}$ linear fluoroalkylene group having at least one hydrogen atom, m1 is an integer of from 0 to 10, provided that when m1 is at least 2, $(R^{f2}O)_{m1}$ may be composed of at least two kinds of $R^{f2}O$ different in either or both of the number of carbon atoms and the number of hydrogen atoms, $R^{f3}$ is a $C_{1-10}$ linear perfluoroalkylene group, m2 is an integer of from 2 to 200, provided that $(R^{f3}O)_{m2}$ may be composed of at least two kinds of $R^{f3}O$ different in the number of carbon atoms, and $R^{f4}$ is a $C_{1-10}$ linear perfluoroalkylene group.

[6] The fluorinated ether compound according to any one of [1] to [4], wherein $R^f$ is a linear perfluoroalkyl group having at least two carbon atoms and having at least one etheric oxygen atoms between carbon-carbon atoms.

[7] The fluorinated ether compound according to any one of [1] to [4], wherein $R^f$ is a group represented by the following formula ($R^f$-1), a group represented by the following formula ($R^f$-2) or a group represented by the following formula ($R^f$-3):

$$R^{f1}O\{(CF_2O)_{m21}(CF_2CF_2O)_{m22}\}CF_2— \qquad (R^f\text{-}1)$$

$$R^{f1}OCHFCF_2OCH_2CF_2O\{(CF_2))_{m21}(CF_2CF_2O)_{m22}\}CF_2— \qquad (R^f\text{-}2)$$

$$R^{f1}O(CF_2CF_2OCF_2CF_2CF_2CF_2O)_{m25}CF_2CF_2OCF_2CF_2CF_2— \qquad (R^f\text{-}3)$$

wherein $R^{f1}$ is a $C_{1-20}$ perfluoroalkyl group, each of m21 and m22 is an integer of at least 1, m21+m22 is an integer of from 2 to 200, provided that each $CF_2O$ and each $CF_2CF_2O$ may be bonded in any order, and m25 is an integer of from 1 to 100.

[8] The fluorinated ether compound according to any one of [1] to [7], which has a number average molecular weight of from 1,000 to 30,000.

[9] A coating liquid comprising the fluorinated ether compound as defined in any one of [1] to [8] and a liquid medium.

[10] An article having a surface layer formed from the fluorinated ether compound as defined in any one of [1] to [8].

[11] A process for producing an article having a surface layer formed from the fluorinated ether compound as defined in any one of [1] to [8], which comprises treating the surface of a substrate with the fluorinated ether compound by dry coating.

[12] A process for producing an article having a surface layer formed from a fluorinated ether compound, which comprises treating the surface of a substrate with the coating liquid as defined in [9] by wet coating.

[13] A compound represented by the following formula (13-1).

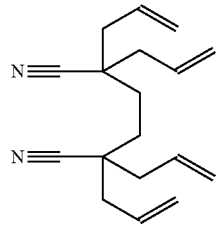

(13-1)

[14] A compound represented by the following formula (14-1).

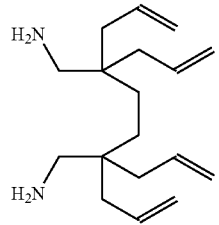

(14-1)

Advantageous Effects of Invention

The fluorinated ether compound and coating liquid of the present invention can form a surface layer excellent in water/oil repellency, abrasion resistance, fingerprint stain removability and lubricity.

The article of the present invention has a surface layer excellent in water/oil repellency, abrasion resistance, fingerprint stain removability and lubricity.

The novel compounds of the present invention are useful as intermediates for production of fluorinated ether compounds.

DESCRIPTION OF EMBODIMENTS

In this specification, a compound represented by the formula (1) will be referred to as compound (1). Compounds represented by other formulae will be referred to in the same manner.

The following terms in this specification have the following meanings.

An "etheric oxygen atom" means an oxygen atom to form an ether bond (—O—) between carbon-carbon atoms. In the chemical formula of an oxyfluoroalkylene group, the oxygen atom is written on the right of the fluoroalkylene group.

A "hydrolyzable silyl group" means a group capable of forming a silanol group (Si—OH) upon hydrolysis. For example, it is $SiR^3{}_nL_{3-n}$ in the formula (1).

A "surface-treated layer" means a layer which is formed on the surface of a substrate.

The "number average molecular weight" of a fluorinated ether compound is measured by NMR spectrometry and calculated as follows.

It is calculated by obtaining the number (average value) of oxyperfluoroalkylene groups by using a terminal group as a standard, by means of $^1$H-NMR and $^{19}$F-NMR. The terminal group is, for example, $R^{f1}$ or $SiR^3{}_nL_{3-n}$ in the formulae.

[Fluorinated Ether Compound]

The fluorinated ether compound of the present invention (hereinafter referred to as the present compound) is compound (1).

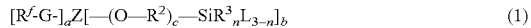

$$[R^f\text{-}G\text{-}]_a Z[\text{—}(O\text{—}R^2)_c\text{—}SiR^3{}_n L_{3-n}]_b \quad (1)$$

In the formula (1), $R^f$ is a linear polyfluoroalkyl group having at least two carbon atoms, which has at least one etheric oxygen between carbon-carbon atoms or has at least one fluorine atoms on a carbon atom bonded to G or Z. G is —$R^1$—O—, —$R^1$—CONH—, —CONH— or a single bond. $R^1$ is an alkylene group. Z is a hydrocarbon group having a valence of (a+b) or a hydrocarbon group having at least two carbon atoms, having at least one etheric oxygen atom between carbon-carbon atoms and having a valence of (a+b). $R^2$ is an alkylene group. $R^3$ is a hydrogen atom or a monovalent hydrocarbon group. L is a hydrolyzable group, n is an integer of from 0 to 2, a is an integer of at least 1, b is an integer of at least 1. (a+b) is at least 3. When a is 1, b is at least 4, and when a is at least 2, b is at least 1. When a is at least 2, each [$R^f$-G-] may be identical with or different from one another. When b is at least 2 each [—(O—$R^2$)$_c$-SiR$^3{}_n$L$_{3-n}$] may be identical with or different from one another, c is 0 or 1.

Because of the presence of $R^f$, compound (1) has a high content of fluorine atoms. Therefore, it can form a surface layer excellent in water/oil repellency, abrasion resistance and fingerprint stain removability.

$R^f$ has a linear structure with no branches. Compound (1) having such a structure can form a surface layer excellent in abrasion resistance and lubricity. In contrast, conventional fluorinated ether compounds having a branched poly (oxyperfluoroalkylene) group form a surface layer with insufficient abrasion resistance and lubricity.

As $R_f$, a linear perfluoroalkyl group having at least two carbon atoms and having at least one etheric oxygen atom between carbon-carbon atoms is favorable to better water/oil repellency, abrasion resistance and fingerprint stain removability of the surface layer.

As $R_f$, a group represented by the following formula ($R^f$-0) is favorable to better water/oil repellency, abrasion resistance, fingerprint stain removability and lubricity of the surface layer.

$$R^{f1}O(R^{f2}O)_{m1}(R^{f3}O)_{m2}R^{f4}\text{—} \quad (R^f\text{-0})$$

In the formula ($R^f$-0), when m1 is 0, $R^{f1}$ is a $C_{1-20}$ linear perfluoroalkyl group, and when m1 is at least 1, $R^{f1}$ is a $C_{1-20}$ linear perfluoroalkyl group or a $C_{2-20}$ linear perfluoroalkyl group having at least one etheric oxygen atom between carbon-carbon atoms. $R^{f2}$ is a $C_{1-10}$ linear fluoroalkylene group having at least one hydrogen atom. m1 is an integer of from 0 to 10. When m1 is at least 2, $(R^{f2}O)_{m1}$ may be composed of at least two kinds of $R^{f2}O$ different in either or both of the number of carbon atoms and the number of hydrogen atoms. $R^{f3}$ is a $C_{1-10}$ linear perfluoroalkylene group. m2 is an integer of from 2 to 200. $(R^{f3}O)_{m2}$ may be composed of at least two kinds of $R^{f3}O$ different in the number of carbon atoms. $R^{f4}$ is a $C_{1-10}$ linear perfluoroalkylene group.

The number of carbon atoms in $R^{f1}$ is preferably from 1 to 6, particularly preferably from 1 to 3, for better lubricity and abrasion resistance of the surface layer.

$R^{f1}$ may be, for example, $CF_3$—, $CF_3CF_2$—, $CF_3CF_2CF_2$—, $CF_3OCF_2CF_2$— (when m1 is at least 1), $CF_3CF_2OCF_2CF_2$— (when m1 is at least 1) or $CF_3CF_2CF_2OCF_2CF_2$— (when m1 is at least 1).

Because $R^{f1}$ terminates in $CF_3$—, compound (1) has $CF_3$— at at least one end. Compound (1) having such a structure forms a surface layer having low surface energy which is excellent in lubricity and abrasion resistance.

The number of hydrogen atoms in $R^{f2}$ is at least 1, preferably at least 2, particularly preferably at least 3 for good appearance of the surface layer. The number of hydrogen atoms in $R^{f2}$ is preferably at most (the number of carbon atoms in $R^{f2}$)×2, particularly preferably at most (the number of carbon atoms in $R^{f2}$) for better water/oil repellency of the surface layer.

The hydrogen-containing $R^{f2}$ makes compound (1) more soluble in a liquid medium and hence makes compound (1) less unlikely to agglomerate in a coating liquid. Because compound (1) is unlikely to agglomerate during drying of a coating liquid applied to a substrate, a surface layer having better appearance is obtained.

The number of carbon atoms in $R^{f2}$ is preferably from 1 to 6, particularly preferably from 1 to 3 for better lubricity and abrasion resistance of the surface layer.

m1 is preferably an integer of from 0 to 5, particularly preferably an integer of from 1 to 3. When m1 is not smaller than the lower limit of the above-mentioned range, the resulting surface layer has good appearance. When m1 is not larger than the upper limit of the above-mentioned range, the resulting surface layer is excellent in water/oil repellency, abrasion resistance, fingerprint stain removability and lubricity.

When $(R^{f2}O)_{m1}$ is composed of at least two kinds of $R^{f2}O$, each $R^{f2}O$ may be bonded in any order without particular restrictions.

$(R^{f2}O)_{m1}$ is preferably a single bond, or a group selected from the groups consisting of —$CHFCF_2OCH_2CF_2O$—, —$CF_2CHFCF_2OCH_2CF_2O$—, $CF_2CF_2CHFCF_2OCH_2CF_2O$— and —$CF_2CH_2OCH_2CF_2O$—, in view of easy production of compound (1).

$R^{f3}$ is preferably a $C_{1-6}$ linear perfluoroalkylene group for better abrasion resistance and lubricity of the surface layer, more preferably a $C_{1-4}$ linear perfluoroalkylene group, particularly preferably a $C_{1-2}$ linear perfluoroalkylene group for better lubricity of the surface layer.

Compound (1) having $(R^{f3}O)_{m2}$ has a higher content of fluorine atoms and hence forms a surface layer having better water/oil repellency, abrasion resistance and fingerprint stain removability.

Because $R^{f3}$ is a linear perfluoroalkylene group, $(R^{f3}O)_{m2}$ has a straight structure. Compound (1) having such a structure forms a surface layer excellent in abrasion resistance and lubricity.

m2 is preferably an integer of from 5 to 150, particularly preferably an integer of from 10 to 100. When m2 is not smaller than the lower limit of the above-mentioned range, the resulting surface layer is excellent in water/oil repellency. When m2 is not larger than the upper limit of the above-mentioned range, the resulting surface layer is excellent in abrasion resistance. Namely, when compound (1) has too large a number average molecular weight, because the number of hydrolyzable silyl groups per a unit molecular weight, abrasion resistance is poor.

When $(R^{f3}O)_{m2}$ is composed of at least two kinds of $R^{f3}O$, each $R^{f3}O$ may be bonded in any order without particular restrictions. For example, in the case of $CF_2O$ and $CF_2CF_2O$, $CF_2O$ and $CF_2CF_2O$ may be arranged randomly, alternately or in blocks.

$(R^{f3}O)_{m2}$ is preferably $\{(CF_2O)_{m21}(CF_2CF-O)_{m22}\}$, $(CF_2CF_2O)_{m23}$, $(CF_2CF_2CF_2O)_{m24}$ or $(CF_2CF_2OCF_2CF_2CF_2CF_2O)_{m25}CF_2CF_2O$, particularly preferably $\{(CF_2O)_{m21}(CF_2CF_2O)_{m22}\}$ or $(CF_2CF_2OCF_2CF_2CF_2CF_2O)_{m25}CF_2CF_2O$ for excellent abrasion resistance, fingerprint stain removability and lubricity of the surface layer.

Herein, m21 is an integer of at least 1, m22 is an integer of at least 1, m21+m22 is an integer of from 2 to 200, provided that each $CF_2O$ and each $CF_2CF_2O$ may be bonded in any order, m23 and m24 are integers of from 2 to 200, and m 25 is an integer of from 1 to 100.

$R^{f4}$ is, for example, —$CF_2$— when $(R^{f3}O)_{m2}$ is $\{(CF_2O)_{m21}(CF_2CF_2O)_{m22}\}$ or $(CF_2CF_2O)_{m23}$, —$CF_2CF_2$— when $(R^{f3}O)_{m2}$ is $(CF_2CF_2CF_2O)_{m24}$, or —$CF_2CF_2CF_2$— when $(R^{f3}O)_{m2}$ is $(CF_2CF_2O—CF_2CF_2CF_2CF_2O)_{m25}$.

Compound (1) having linear $R^{f4}$ forms a surface layer excellent in abrasion resistance and lubricity.

The group represented by the formula ($R^{f}$-0) is preferably a group represented by the following formula ($R^{f}$-1), a group represented by the following formula ($R^{f}$-2) or a group represented by the following formula ($R^{f}$-3) in view of excellent water/oil repellency, abrasion resistance, fingerprint stain removability, lubricity and appearance of the surface layer and easy production of compound (1).

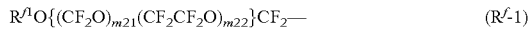  ($R^{f}$-1)

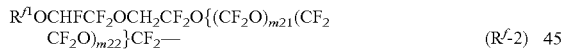  ($R^{f}$-2)

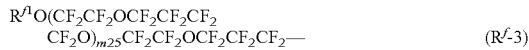  ($R^{f}$-3)

In the formulae ($R^{f}$-1) to ($R^{f}$-3), $R^{f1}$ is a $C_{1-20}$ linear perfluoroalkyl group, each of m21 and m22 is an integer of at least 1, m21+m22 is an integer of from 2 to 200, provided that each $CF_2$ and each $CF_2CF_2O$ may be bonded in any order, and m25 is an integer of from 1 to 100.

G is —$R^1$—O—, —$R^1$—CONH—, —CONH— or a single bond.

G is preferably —$R^1$—CONH— or —CONH— in view of excellent light resistance of compound (1), or preferably —$R^1$—O— in view of excellent chemical resistance of compound (1).

$R^1$ is an alkylene group.

$R^1$ is preferably a $C_{1-4}$ alkylene group, particularly preferably —$CH_2$— in view of easy production of compound (1).

Z is a hydrocarbon group having a valence of (a+b) or a hydrocarbon group having at least two carbon atoms, having at least one etheric oxygen atom between carbon-carbon atoms and having a valence of (a+b). Z is a group derived from a polyhydric alcohol having (a+b) hydroxyl groups by removal of hydroxyl groups when G is —$R^1$—O— and cis 1.

As Z, groups of the following formulae may, for example, be mentioned.

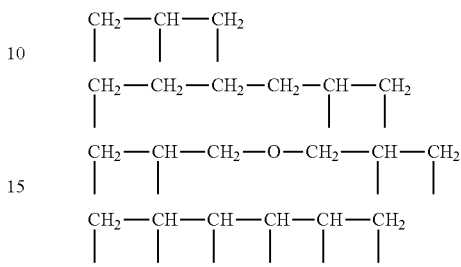

Z is preferably a group derived from a polyhydric alcohol having primary hydroxyl groups by removal of the hydroxyl groups in view of excellent reactivity of hydroxyl groups.

Z is particularly preferably a group represented by the following formula (Z-1), a group represented by the following formula (Z-2), a group represented by the following formula (Z-3), a group represented by the following formula (Z-4) or a group represented by the following formula (Z-5) wherein $R^4$ is an alkyl group, preferably a methyl group or an ethyl group, in view of availability of the raw material.

  (Z-1)

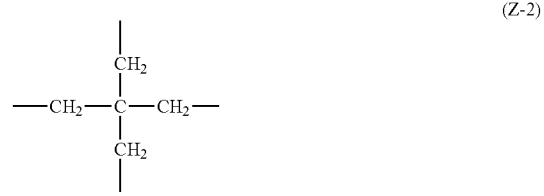  (Z-2)

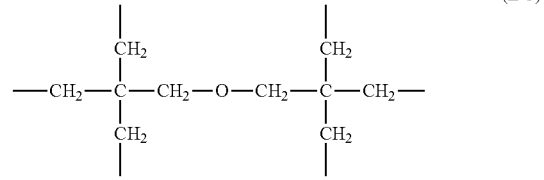  (Z-3)

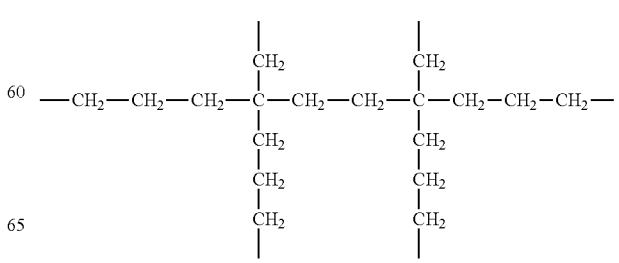  (Z-4)

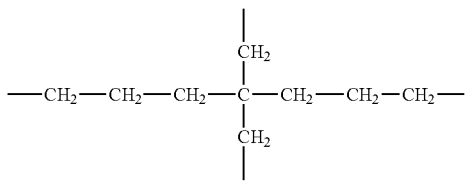

R² is an alkylene group.

R² is preferably a C$_{4-14}$ alkylene group for easy production of compound (1), particularly preferably C$_{4-10}$ alkylene group in view of suppressing formation of a by-product through isomerization of some or all of the allyl group (—CH$_2$CH═CH$_2$) into an inner olefin (—CH═CHCH$_3$) accompanying hydrosilylation during the production of compound (1) described later.

SiR$^3{}_n$L$_{3-n}$ is a hydrolyzable silyl group.

Compound (1) has a terminal hydrolyzable silyl group. Compound (1) having such a structure forms a firm bond with a substrate.

L is a hydrolyzable group, which is capable of forming a hydroxyl group upon hydrolysis. Namely, the terminal Si-L group in compound (1) turns into a silanol group (Si—OH) upon hydrolysis. The silanol group further reacts intermolecularly to form a Si—O—Si linkage. The silanol group also undergoes dehydration condensation with a hydroxyl group on the surface of a substrate to form a chemical bond (substrate-O—Si).

L may, for example, be an alkoxy group, a halogen atom, an acyl group or an isocyanato group (—NCO). The alkoxy group is preferably a C$_{1-4}$ alkoxy group.

L is preferably a C$_{1-4}$ alkoxy group or a halogen atom in view of easy production of compound (1). As the halogen atom, a chlorine atom is particularly preferred. L is preferably a C$_{1-4}$ alkoxy group for less outgassing during coating and excellent storage stability of compound (1), and particularly preferably an ethoxy group for long-lasting storage stability of compound (1), or a methoxy group for a shorter reaction time after coating.

R³ is a hydrogen atom or a monovalent hydrocarbon group. The monovalent hydrocarbon group may, for example, be an alkyl group, a cycloalkyl group, an alkenyl group or an allyl group. The number of carbon atoms in the monovalent hydrocarbon group is preferably from 1 to 6, more preferably from 1 to 3, particularly preferably 1 or 2. When the number of carbon atoms in R³ is within this range, compound (1) is easy to produce.

n is preferably 0 or 1, particularly preferably 0. The presence of a plurality of L in one hydrolyzable silyl group enables formation of a strong bond with a substrate.

SiR$^3{}_n$L$_{3-n}$ is preferably Si(OCH$_3$)$_3$, SiCH$_3$(OCH$_3$)$_2$, Si(OCH$_2$CH$_3$)$_3$, SiCl$_3$, Si(OCOCH$_3$)$_3$ or Si(NCO)$_3$. Si(OCH$_3$)$_3$ is particularly preferred in view of easy handling in industrial production.

a is preferably from 1 to 10, particularly preferably from 1 to 4. When a is not smaller than the lower limit of the above-mentioned range, the resulting surface layer is excellent in water/oil repellency, abrasion resistance, fingerprint stain removability and lubricity. When a is not larger than the upper limit of the above-mentioned range, the resulting surface layer has good appearance.

(a+b) is preferably from 3 to 15, particularly preferably from 3 to 12.

When a is 1, b is at least 4, preferably from 4 to 10, particularly preferably from 4 to 5. When a is 1, if b is below 4, the surface layer will have insufficient abrasion resistance. If b is not larger than the upper limit of the above-mentioned range, the resulting surface layer has good appearance, and compound (1) has excellent storage stability.

When a is an integer of at least 2, b is an integer of at least 1, preferably an integer of from 1 to 10, particularly preferably an integer of from 1 to 4. When a is an integer of at least 2, the resulting surface layer will have a high density of R$^f$—R$^1$—O— groups and excellent lubricity, and hence is antifrictional. Therefore, even when b is 1, the surface layer will have excellent abrasion resistance. When b is not larger than the upper limit of the above-mentioned range, the resulting surface layer has good appearance, and compound (1) has excellent storage stability.

When a is at least 2, each [R$^f$-G-] may be identical with or different from one another.

When b is at least 2, each [—(O—R²)$_c$—SiR$^3{}_n$L$_{3-n}$] may be identical with or different from one another.

c is 0 or 1. c is preferably 0 in view of excellent light resistance of compound (1) or preferably 1 in view of easy production of compound (1).

As compound (1), preferred are compounds (1-1) to (1-8) of the following formulae because they are easy to produce industrially and handle and capable of forming a surface layer excellent in water/oil repellency, abrasion resistance, fingerprint stain removability, lubricity and appearance.

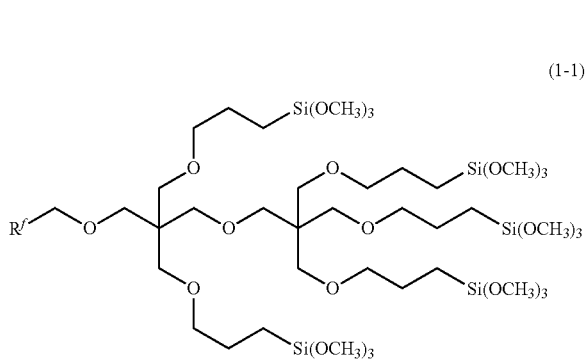

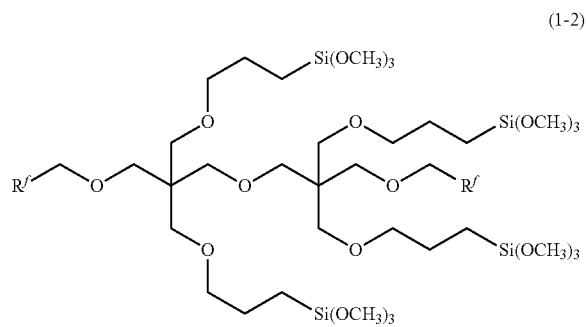

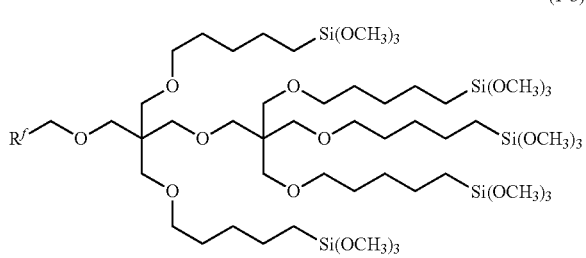

-continued (1-4)
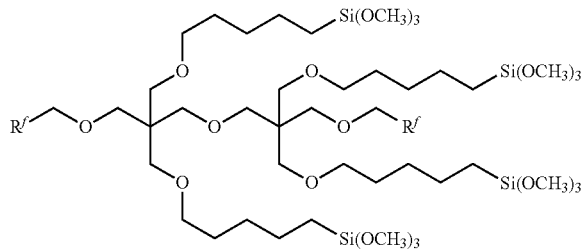

(1-5)
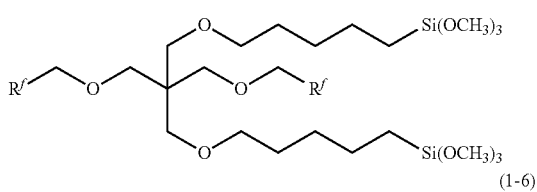

(1-6)
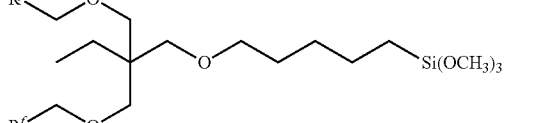

(1-7)
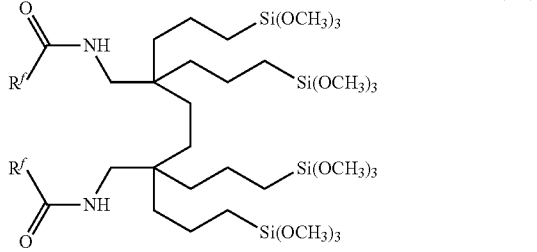

(1-8)
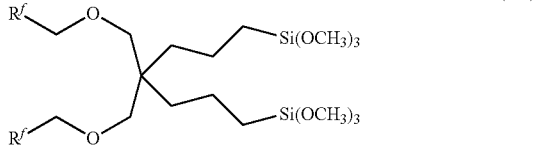

Compound (1) represented by $[R^f-R^1-O-]_aZ[-O-R^2-SiR^3{}_nL_{3-n}]_b$ is produced, for example, as described below.

Compound (2) and compound (3) are reacted in the presence of a basic compound to obtain a crude product comprising plural kinds of compound (4) different in the ratio of a to b, and from the crude product, compound (4) having a given ratio of a to b is separated by a known means (such as column purification).

$$Z(OH)_{a+b} \quad (2)$$

$$X^1-R^{21}-CH=CH_2 \quad (3)$$

$$[HO-]_aZ[-O-R^{21}CH=CH_2]_b \quad (4)$$

Herein, $X^1$ is a halogen atom, and $R^{21}$ is an alkylene group having fewer carbon atoms than $R^2$ by two.

Compound (4) is reacted with trifluoromethanesulfonic anhydride in the presence of a basic compound such as 2,6-lutidine to obtain compound (5).

$$[F_3C-SO_2-O-]_aZ[-O-R^{21}-CH=CH_2]_b \quad (5)$$

Compound (5) and compound (6) are reacted in the presence of a basic compound to obtain compound (7).

$$R^f-R^1-OH \quad (6)$$

$$[R^f-R^1-O-]_aZ[-O-R^2-SiR^3{}_nL_{3-n}]_b \quad (7)$$

Compound (7) is hydrosilylated with compound (8), preferably by using a transition metal catalyst such as platinum or a radical generator such as an organic peroxide, to obtain compound (1).

$$HSiR^3{}_nL_{3-n} \quad (8)$$

$$[R^f-R^1-O-]_aZ[-O-R^2-SiR^3{}_nL_{3-n}]_b \quad (1)$$

As compound (2) wherein a+b is 3, glycerin, trimethylolethane, trimethylolpropane, 1,2,6-hexanetriol or the like may be mentioned.

As compound (2) wherein a+b is 4, diglycerin, pentaerythritol, ditrimethylolpropane or the like may be mentioned.

As compound (2) wherein a+b is 6, dipentaerythritol, sorbitol, mannitol, dulcitol or the like may be mentioned.

As compound (3), allyl bromide, 5-bromo-1-pentene or the like may be mentioned.

Compound (6) is produced, for example, as described in WO2013/121984, WO2014/163004, WO2015/087902 or the like.

As compound (8), trimethoxysilane, triethoxysilane, methyldimethoxysilane, trichlorosilane or the like may be mentioned.

With appropriate choice of compound (2), compound (3), compound (6) and compound (8) and the ratio of a to b in compound (4), it is possible to produce compound (1) of interest by conducting each reaction as described later in the Examples.

Compound (1) represented by $[R^f-CONH-]_aZ[-SiR^3{}_nL_{3-n}]_b$ is produced, for example, as described below.

Compound (12) and compound (3) are reacted in the presence of a basic compound to obtain compound (13).

$$NC-(CH_2)_2-CN \quad (12)$$

$$X^1-R^{21}CH=CH_2 \quad (3)$$

$$NC-C(-R^{21}-CH=CH_2)_2-(CH_2)_{d-2}-C(-R^{21}-CH=CH_2)_2-CN \quad (13)$$

Herein, d is an integer of at least 2, $X^1$ is a halogen atom, and $R^{21}$ is an alkylene group.

Compound (13) is reduced to compound (14).

$$NH_2CH_2-C(-R^{21}-CH=CH_2)_2-(CH_2)_{d-2}-C(-R^{21}-CH=CH_2)_2-CH_2NH_2 \quad (14)$$

Compound (14) and compound (15) are reacted in the presence of a basic compound to obtain compound (16).

$$R^f-COX^2 \quad (15)$$

$$R^f-CONH-CH_2-C(-R^{21}-CH=CH_2)_2-(CH_2)_{d-2}-C(-R^{21}-CH=CH_2)_2-CH_2-NHCO-R^f \quad (16)$$

Herein, $X^2$ is a halogen atom or an alkoxy group.

Compound (16) is hydrosililayed with compound (8), preferably by using a transition metal catalyst such as platinum or a radical generator such as an organic peroxide, to obtain compound (1).

$$R^f-CONH-CH_2-C(-R^{21}-CH_2CH_2-SiR^3{}_nL_{3-n})_2-(CH_2)_{d-2}-C(-R^{21}-CH_2CH_2-SiR^3{}_nL_{3-n})_2-CH_2-NHCO-R^f \quad (1)$$

As compound (12), succinonitrile (d=2), glutaronitrile (d=3), diponitrile (d=4), pimelonitrile (d=5) or the like may be mentioned.

Compound (15) is produced, for example, as described in WO2013/121984 or the like.

Compound (1) represented by $[R^f—R^1—O—]_aZ[—SiR^3{}_nL_{3-n}]_b$ is produced, for example, as described below.

Compound (17) is reacted with trifluoromethansulfonic anhydride in the presence of a basic compound such as 2,6-lutidine to obtain compound (18).

(HO—CH$_2$—)$_2$C(—R$^{22}$—CH=CH$_2$)$_2$ (17)

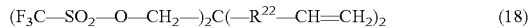

(F$_3$C—SO$_2$—O—CH$_2$—)$_2$C(—R$^{22}$—CH=CH$_2$)$_2$ (18)

Herein, R$^{22}$ is an alkylene group.

Compound (18) and compound (6) are reacted in the presence of a basic compound to obtain compound (19).

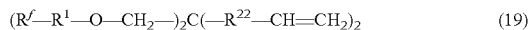

(R$^f$—R$^1$—O—CH$_2$—)$_2$C(—R$^{22}$—CH=CH$_2$)$_2$ (19)

Compound (19) is hydrosilylated with compound (8), preferably by using a transition metal catalyst such as platinum or a radical generator such as an organic peroxide, to obtain compound (1).

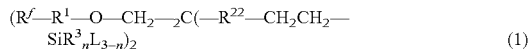

(R$^f$—R$^1$—O—CH$_2$—)$_2$C(—R$^{22}$—CH$_2$CH$_2$—SiR$^3{}_nL_{3-n}$)$_2$ (1)

As compound (17), 2,2-diallyl-1,3-propanediol or the like may be mentioned.

The present compound may be a single compound composed of one kind of compound (1) or a mixture of two or more kinds of compound (1) different in R$^f$, R$^1$, Z, R$^2$, SiR$^3{}_nL_{3-n}$, a, b, c or the like.

In the present invention, a single compound means that compound (1) is composed of compounds which are identical except for the number of oxyfluoroperfluoroalkylene groups in R$^f$. For example, when R$^f$ is (R$^f$-1), compound (1) is usually produced as a mixture of plural kinds of compound (1) different in m21 and m22. In this case, a series of compounds having certain m21 and m22 distributions are considered as a single kind of compound (1).

The number average molecular weight of the present compound is preferably from 1,000 to 30,000, more preferably from 2,000 to 25,000, particularly preferably from 3,000 to 20,000. When the number average molecular weight of the present compound is within the above-mentioned range, the resulting surface layer is excellent in abrasion resistance.

[Fluorinated Ether Composition]

The fluorinated ether composition of the present invention (hereinafter referred to also as the present composition) is a composition comprising compound (1) and at least one of a fluorinated ether compound other than compound (1) and impurities described below. The impurities may, for example, be compounds unavoidable in production of the present compound and other fluorinated ether compounds. The present composition does not contain the liquid medium described later.

As the other fluorinated ether compounds, fluorinated ether compounds produced as by-products during production of compound (1) and known fluorinated ether compounds used in the same applications as compound (1) may be mentioned.

The other fluorinated ether compounds are preferably those unlikely to impair the properties of compound (1).

The other fluorinated ether compounds are preferably contained in such an amount that they are unlikely to impair the properties of compound (1).

As the fluorinated ether compounds produced as by-products, fluorinated ether compounds having unreacted hydroxyl groups derived from compound (2) and fluorinated ether compounds formed through isomerization of some of the allyl groups into an inner olefin accompanying hydrosilylation during the production of compound (1) may, for example, be mentioned. When the present composition contains fluorinated ether compounds produced as by-products, the fluorinated ether compounds produced as by-products can be removed or decreased by a simple purification step.

As the known fluorinated ether compounds, commercially available fluorinated ether compounds may, for example, be mentioned. When the present composition contains known fluorinated ether compounds, they may have new effects such as compensation for the properties of compound (1).

The proportion of the present compound in the present composition is less than 100 mass % and at least 60 mass %, preferably at least 70 mass %, particularly at least 80 mass %.

When the present composition contains other fluorinated ether compounds, the proportion of the other fluorinated ether compounds to the total amount of the present compound and the other fluorinated ether compounds in the present composition is preferably at most 40 mass %, more preferably at most 30 mass %, particularly preferably at most 20 mass %.

The total proportion of the present compound and the other fluorinated ether compounds in the present composition is preferably at least 80 mass %, particularly preferably at least 85 mass %.

When the total content of the present compound and the fluorinated ether compounds other than compound (1) is within the above-mentioned range, the resulting surface layer is excellent in water/oil repellency, abrasion resistance, fingerprint stain removability, lubricity and appearance.

[Coating Liquid]

The coating liquid of the present invention (hereinafter referred to also as the present coating liquid) comprises the present compound or the present composition, and a liquid medium. The present coating liquid may be any liquid and may be a solution or a dispersion.

The present coating liquid contains the present compound or the present composition and may contain impurities such as by-products formed during production of the present compound.

The concentration of the present compound or the present composition in the present coating liquid is preferably from 0.001 to 10 mass %, particularly preferably from 0.1 to 1 mass %.

The liquid medium is preferably an organic solvent. The organic solvent may be a fluorinated organic solvent or a non-fluorinated organic solvent, or may contain both solvents.

The fluorinated organic solvent may, for example, be a fluorinated alkane, a fluorinated aromatic compound, a fluoroalkyl ether, a fluorinated alkylamine or a fluoroalcohol.

The fluorinated alkane is preferably a C$_{4-8}$ compound. As commercially available products, for example, C$_6$F$_{13}$H (ASAHIKLIN (registered trademark) AC-2000, manufactured by Asahi Glass Company, Limited), C$_6$F$_{13}$C$_2$H$_5$ (ASAHIKLIN (registered trademark) AC-6000, manufactured by Asahi Glass Company, Limited) and C$_2$F$_5$CHFCHFCF$_3$ (Vertrel (registered trademark) XF, manufactured by The Chemours Company) may, for example, be mentioned.

The fluorinated aromatic compound may, for example, be hexafluorobenzene, trifluoromethylbenzene, perfluorotoluene or bis(trifluoromethyl)benzene.

The fluoroalkyl ether is preferably a $C_{4-12}$ compound. As commercially available products, for example, $CF_3CH_2OCF_2CF_2H$ (ASAHIKLIN (registered trademark) AE-3000, manufactured by Asahi Glass Company, Limited), $C_4F_9OCH_3$ (Novec (registered trademark) 7100, manufactured by Sumitomo 3M Limited), $C_4F_9OC_2H_5$ (Novec (registered trademark) 7200, manufactured by Sumitomo 3M Limited) and $C_6F_{13}OCH_3$ (Novec (registered trademark) 7300, manufactured by Sumitomo 3M Limited) may, for example, be mentioned.

The fluorinated alkylamine may, for example, be perfluorotripropylamine or perfluorotributylamine.

The fluoroalcohol may, for example, be 2,2,3,3-tetrafluoropropanol, 2,2,2-trifluoroethanol or hexafluoroisopropanol.

The non-fluorinated organic solvent is preferably a compound composed solely of hydrogen atoms and carbon atoms or a compound composed solely of hydrogen atoms, carbon atoms and oxygen atoms, and may, for example, be a hydrocarbon organic solvent, an alcohol organic solvent, a ketone organic solvent, an ether organic solvent or an ester organic solvent.

The present coating liquid contains preferably from 90 to 99.999 mass %, particularly preferably from 99 to 99.99 mass %, of the liquid medium.

The present coating liquid may contain other components in addition to the present compound or the present composition and the liquid medium, within a range not to impair the effects of the present invention.

Such other components may, for example, be known additives such as an acid catalyst or a basic catalyst, which promotes hydrolysis of the hydrolyzable silyl group and a condensation reaction, etc.

In the present coating liquid, the content of other components is preferably at most 10 mass %, particularly preferably at most 1 mass %.

The total concentration of the present compound and other components or the total content of the present composition and other components (hereinafter referred to also as solid content) in the present coating liquid is preferably from 0.001 to 10 mass %, particularly preferably from 0.01 to 1 mass %. The solid content of the coating liquid is a value calculated from the mass of the coating liquid before and after 4 hours of heating at 120° C. with a convection dryer.

[Article]

The article of the present invention comprises a substrate and a surface layer formed on the substrate from the present compound or the present composition.

According to the present compound or the present composition, the hydrolyzable silyl groups ($SiR^3{}_nL_{3-n}$) in the present compound hydrolyze into silanol groups (Si—OH), and the silanol groups react intermolecularly to form Si—O—Si linkages or undergo dehydration condensation with hydroxyl groups on the surface of a substrate to form chemical bonds (substrate-O—Si). Namely, the surface layer of the present invention contains all or some of the hydrolyzable silyl groups of the present compound in the hydrolyzed form.

The surface layer is preferably from 1 to 100 nm thick, particularly preferably from 1 to 50 nm thick. The thickness of the surface layer is not lower than the lower limit of the above-mentioned range, surface treatment is likely to have sufficient effect. When the thickness of the surface layer is not higher than the upper limit of the above-mentioned range, utilization efficiency will be high. The thickness of the surface layer can be calculated from the oscillation period of an interference pattern of reflected X-ray measured by X-ray reflectivity with an X-ray diffractometer ATX-G (manufactured by Rigaku Corporation).

The substrate in the present invention is not particularly limited so long as water/oil repellency is desirable for it. The material for the substrate may, for example, be metal, resin, glass, sapphire, ceramics, stone or a composite material thereof.

The substrate is preferably a touch panel substrate or a display substrate, particularly preferably a touch panel substrate. A touch panel substrate is light-transmitting. Here "light-transmitting" means that transmittance of visible light incident from the normal direction in accordance with JIS R3106: 1998 (ISO 9050: 1990) is at least 25%. The material for the touch panel substrate is preferably glass or transparent resin.

The article of the present invention can be produced, for example, by the following methods.

A method for producing the present article, which comprises treating the surface of a substrate with the present compound or the present composition by dry coating.

A method for producing the present article, which comprises applying the present coating liquid to the surface of a substrate by wet coating and drying the coating liquid.

The present compound and the present composition can be used for dry coating directly. The present compound and the present composition are suitable for forming a surface layer having excellent adhesion by dry coating. As dry coating techniques, vacuum vapor deposition, CVD, sputtering or the like may be mentioned. With a view to suppressing decomposition of the present compound and in view of simplicity of apparatus, vacuum vapor deposition can be suitably used.

As techniques for wet coating, spin coating, wipe coating, spray coating, squeegee coating, dip coating, die coating, ink-jet coating, flow coating, roll coating, casting, a Langmuir-Blodgett deposition, gravure coating or the like may be mentioned.

In order to improve the abrasion resistance of the surface layer, if necessary, an operation for promoting the reaction between the present compound and the substrate may be carried out. As such an operation, heating, humidification or light irradiation may, for example, be mentioned. For example, by heating a substrate having a surface layer formed, in a moisture-containing, it is possible to accelerate a reaction such as hydrolysis of hydrolyzable silyl groups to silanol groups, a reaction of the silanol groups and hydroxy groups on the substrate surface, or formation of a siloxane bond by a condensation reaction of silanol groups.

After the surface treatment, even a compound in the surface layer which are chemically bonded to another compounds or the substrate may be removed as the case requires, specifically speaking, by washing the surface layer with a solvent or wiping the surface layer with cloth wetted with a solvent.

The present article is used as a component or part of products such as optical products, touch panels, anti-reflection film, anti-reflection glass, $SiO_2$-treated glass, tempered glass, sapphire glass, quartz substrate and metal molds.

Products: car navigation systems, mobile phones, digital cameras, digital videos, cameras, portable digital assistants (PDA), portable audio players, car audio systems, game consoles, eyeglasses, camera lenses, lens filters, sunglasses, medical devices (such as gastrocameras), photocopiers, personal computers (PC), liquid crystal displays, organic EL displays, plasma displays, touch panel displays, protective films, anti-reflection films, anti-reflection glass, nanoimprint templates, molds and the like.

EXAMPLES

Now, the present invention will be described in further detail with reference to Examples, but the present invention is not limited to these Examples.

Hereinafter, "%" is "mass %" unless otherwise specified. A mixture composed of two or more kinds of compound (1) is referred to as a "compound", and a mixture of compound (1) and other fluorinated ether compounds is referred to as a "composition".

Ex. 1 to 13, 16 to 30, 22 and 34 are Examples of the present invention, and Ex. 12, 15, 31 and 32 are Comparative Examples.

[Raw Materials]

As compounds (2), the following compounds were obtained.

Compound (2-1): dipentaerythritol (manufactured by ACROS Organics)

Compound (2-2): pentaerythritol (manufactured by KANTO CHEMICAL CO., INC.)

Compound (2-3): trimethylolpropane (manufactured by TOKYO CHEMICAL INDUSTRY CO., LTD.)

As compound (3), the following compounds were obtained.

Compound (3-1): allyl bromide (manufactured by TOKYO CHEMICAL INDUSTRY CO., LTD.)

Compound (3-2): 5-bromo-1-pentene (manufactured by TOKYO CHEMICAL INDUSTRY CO., LTD.)

As compound (6), the following compounds were obtained.

Compound (6-1a): compound obtained in accordance with Preparation Example 6 of WO2015/087902.

$$CF_3CF_2CF_2O\{(CF_2O)_{m21}(CF_2CF_2O)_{m22}\}CF_2-CH_2-OH \quad (6\text{-}1a)$$

wherein average m21: 21, average m22; 20, and the number average molecular weight: 4,200.

Compound (6-1b): compound obtained in accordance with Preparation Example 4 of WO2015/087902.

$$CF_3CF_2CF_2OCHFCF_2OCH_2CF_2O\{(CF_2O)_{m21}(CF_2CF_2O)_{m22}\}CF_2-CH_2-OH \quad (6\text{-}1b)$$

wherein average m21: 21, average 22: 20, and the number average molecular weight: 4,150.

Compound (6-1c): compound obtained in accordance with Example 7 of WO2013/121984.

$$CF_3O(CF_2CF_2OCF_2CF_2CF_2CF_2O)_{m25}CF_2CF_2OCF_2CF_2CF_2-CH_2-OH \quad (6\text{-}1c)$$

wherein average m25: 13, and the number average molecular weight: 4,700.

As compound (8), the following compound was obtained.

Compound (8-1): trimethoxysilane (manufactured by TOKYO CHEMICAL INDUSTRY CO., LTD.)

As fluorinated alcohols other than compound (6), the following compounds were obtained.

Compound (9-1): FLUOROLINK (registered trademark) D4000, manufactured by Solvay)

$$HO-CH_2-CF_2O\{(CF_2O)_{m21}(CF_2CF_2O)_{m22}\}CF_2-CH_2-OH \quad (9\text{-}1)$$

wherein average m21: 21, and average m22: 20.

Compound (9-2): manufactured by Syn Quest Lbs, Inc.

$$CF_3CF_2CF_2O(CF(CF_3)CF_2O)_{m26}CF(CF_3)-CH_2-OH \quad (9\text{-}2)$$

wherein average m26: 6.

As compound (12), the following compound was obtained.

Compound (12-1): adiponitrile (manufactured by TOKYO CHEMICAL INDUSTRY CO., LTD.)

As compound (15), the following compound was obtained.

Compound (15-1c): compound prepared in accordance with Example 6 of WO013/121984.

$$CF_3O(CF_2CF_2OCF_2CF_2CF_2CF_2O)_{m25}CF_2CF_2OCF_2CF_2CF_2-COOCH_3 \quad (15\text{-}1c)$$

wherein average m25: 13, and the number average molecular weight: 4,700.

As compound (17), the following compound was obtained.

Compound (17-1): 2,2-diallyl-1,3-propanediol (prepared from diethyl diallylmalonate (manufactured by TOKYO CHEMICAL INDUSTRY CO., LTD.) in accordance with Journal of the American Chemical Society, 135(7), 2635-2640 (2013).

In the Examples, compound (1-1) having $R^f$ represented by the formula ($R^f$-1) is referred to as compound (1-1a), compound (1-1) having $R^f$ represented by the formula ($R^f$-2) is referred to as compound (1-1b), and compound (1-1) having $R^f$ represented by the formula ($R^f$-3) is referred to as compound (1-1c). Such compounds (1-3) to (1-8), compound (6-1), compound (7-1), compound (15-1), compound (16-1) and compound (19-1) are referred to in the same manner.

Ex. 1

Production of Compound (1-1) Having $R^f$ Represented by the Formula (Rf-1) (Compound (1-1a))

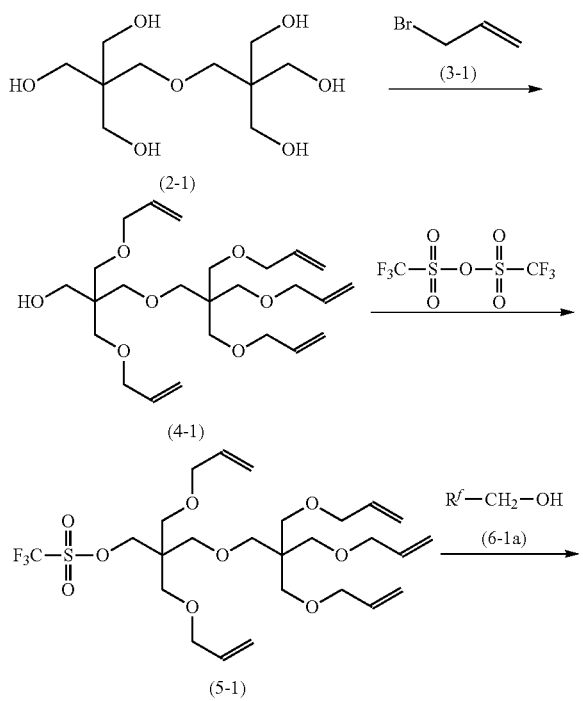

-continued

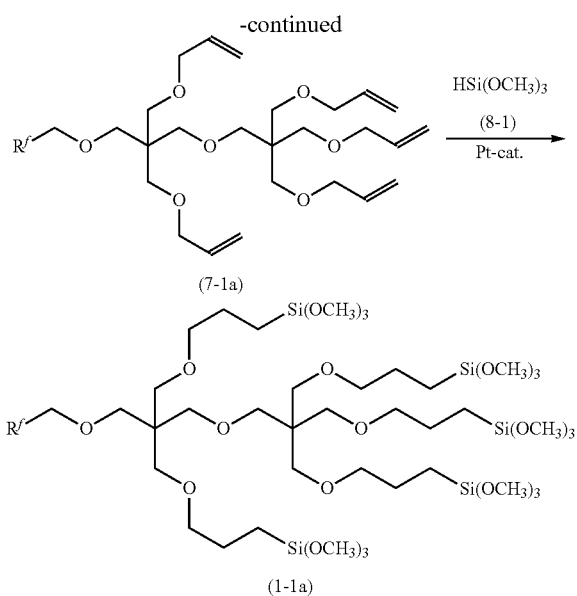

(7-1a)

(1-1a)

Into a 300 mL three-necked flask, 10 g of compound (2-1), 46 g of 48% aqueous KOH and 90 g of dimethyl sulfoxide were heated to 40° C. and stirred with 28.5 g of compound (3-1) for 4 hours. The reaction solution was washed with dilute aqueous hydrochloric acid once, then 200 g of $CF_3CH_2OCF_2CF_2H$ (ASAHIKLIN (registered trademark) AB-300, manufactured by Asahi Glass Company, Limited) (hereinafter referred to also as AE-3000)) was added, and the organic phase was recovered. The recovered solution was concentrated in an evaporator to obtain 15.7 g of a crude product. The crude product was separated by silica gel column chromatography to obtain 3.6 g of compound (4-1).

In a 50 mL two-necked recovery flask, 1 g of compound (4-1), 0.6 g of 2,6-lutidine and 5 g of AE-3000 were stirred with cooling on an ice bath, while trifluoromethanesulfonic anhydride was gradually added dropwise under a nitrogen atmosphere. After another 1 hour of stirring, the reaction solution was washed with dilute aqueous hydrochloric acid, and the recovered organic phase was recovered. The recovered organic phase was concentrated in an evaporator to obtain a crude product. The crude product was separated by silica gel chromatography to obtain 1.2 g of compound (5-1).

In 50 mL two-necked recovery flask, 1.0 g of compound (5-1), 6.6 g of compound (6-1a), 2.7 g of cesium carbonate and 6.6 g of AE-300 were stirred at 80° C. for 4 hours under reflux. After addition of 10 g of AE-3000, the reaction mixture was washed with dilute aqueous hydrochloric acid once, and the organic phase was recovered. The recovered solution was concentrated in an evaporator to obtain a crude product. The crude product was separated by silica gel column chromatography to obtain 6.6 g of compound (7-1a).

In a 100 mL recovery flask made of a tetrafluoroethylene-perfluoro(alkoxy vinyl ether) copolymer, 6.0 g of compound (7-1a), 0.03 g of a xylene solution of platinum/1,3-divinyl-1,1,3,3-tetramethyldisiloxane complex (platinum content: 2%), 1.2 g of compound (8-1), 0.01 g of dimethyl sulfoxide and 0.9 g of 1,3-bis(trifluoromethyl)benzene were stirred at 40° C. for 4 hours. The solvent was distilled off under reduced pressure, and the residue was filtered through a membrane filter having a pore size of 0.2 μm to obtain 6.4 g of composition (A) comprising compound (1-1-1a) resulting from hydrosilylation of the 5 allyl groups in compound (7-1a) and by-products resulting from isomerization of some or all of the 5 allyl groups in compound (7-1a) into an inner olefin (—CH═CHCH$_3$). The hydrosilylation proceeded with a 100% conversion, leaving none of compound (7-1a), and with a 82% selectivity for hydrosilylation.

Ex. 2 to 15

Compound (1) or compositions containing compound (1) or compositions containing comparative compound (11) were obtained in the same manner as Ex. 1 except that compound (2), compound (3) and compound (6) as raw materials were changed to those shown in Table 1, compound (4) was collected with the ratio of a to b shown in Table 1, and the amount of each compound in moles was varied in accordance with the number of reactive functional groups in it. The structures of compound (1) and compound (11) are shown in Table 1.

TABLE 1

| | Raw material/intermediate | | | | | | | Compound (1)/compound (11) | | | |
|---|---|---|---|---|---|---|---|---|---|---|---|
| | Kind of compound | Kind of compound | Compound (4) | | | Kind of compound | Kind of compound | | | Structure | |
| Ex. | (2) | (3) | Kind | a | b | (6) | (8) | Kind | Formula | Kind of $R^{f1}$/Q | Terminal $R^{f1}$ in $R^f$ |
| 1 | (2-1) | (3-1) | (4-1) | 1 | 5 | (6-1a) | (8-1) | (1-1a) | (1-1) | ($R^f$-1) | $CF_3CF_2CF_2$— |
| 2 | (2-1) | (3-1) | (4-1) | 1 | 5 | (6-1b) | (8-1) | (1-1b) | (1-1) | ($R^f$-2) | $CF_3CF_2CF_2$— |
| 3 | (2-1) | (3-1) | (4-1) | 1 | 5 | (6-1c) | (8-1) | (1-1c) | (1-1) | ($R^f$-3) | $CF_3$— |
| 4 | (2-1) | (3-2) | (4-3) | 1 | 5 | (6-1a) | (8-1) | (1-3a) | (1-3) | ($R^f$-1) | $CF_3CF_2CF_2$— |
| 5 | (2-1) | (3-2) | (4-3) | 1 | 5 | (6-1b) | (8-1) | (1-3b) | (1-3) | ($R^f$-2) | $CF_3CF_2CF_2$— |
| 6 | (2-1) | (3-2) | (4-3) | 1 | 5 | (6-1c) | (8-1) | (1-3c) | (1-3) | ($R^f$-3) | $CF_3$— |
| 7 | (2-1) | (3-2) | (4-4) | 2 | 4 | (6-1a) | (8-1) | (1-4a) | (1-4) | ($R^f$-1) | $CF_3CF_2CF_2$— |
| 8 | (2-1) | (3-2) | (4-4) | 2 | 4 | (6-1b) | (8-1) | (1-4b) | (1-4) | ($R^f$-2) | $CF_3CF_2CF_2$— |
| 9 | (2-1) | (3-2) | (4-4) | 2 | 4 | (6-1c) | (8-1) | (1-4c) | (1-4) | ($R^f$-3) | $CF_3$— |
| 10 | (2-2) | (3-2) | (4-5) | 2 | 2 | (6-1a) | (8-1) | (1-5a) | (1-5) | ($R^f$-1) | $CF_3CF_2CF_2$— |
| 11 | (2-2) | (3-2) | (4-5) | 2 | 2 | (6-1c) | (8-1) | (1-5c) | (1-5) | ($R^f$-3) | $CF_3$— |
| 12 | (2-3) | (3-2) | (4-6) | 2 | 1 | (6-1a) | (8-1) | (1-6a) | (1-6) | ($R^f$-1) | $CF_3CF_2CF_2$— |
| 13 | (2-3) | (3-2) | (4-6) | 2 | 1 | (6-1c) | (8-1) | (1-6c) | (1-6) | ($R^f$-3) | $CF_3$— |
| 14 | (2-1) | (3-1) | (4-1) | 1 | 5 | (9-1) | (8-1) | (11-1) | (11-1) | (Q) | — |
| 15 | (2-1) | (3-1) | (4-1) | 1 | 5 | (9-2) | (8-1) | (11-2) | (1-1) | ($R^f$-4) | $CF_3CF_2CF_2$— |

Compounds (4-3) to (4-6) in the table are represented by the following formulae.

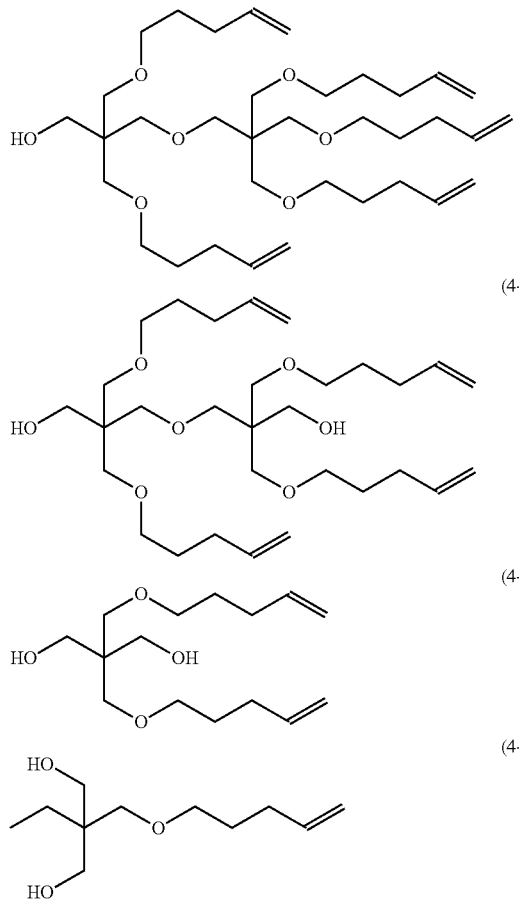

(4-3)
(4-4)
(4-5)
(4-6)

Compounds (1-1) to (1-6) in the table are previously shown.

Compound (11-i) in the table is represented by the following formula.

The NMR spectrum data of compound (1) and compound (11) are shown below.

NMR spectrum of compound (1-1a)
$^1$H-NMR (300.4 MHz, solvent: CDCl$_3$, standard: tetramethylsilane (TMS)) δ (ppm): 0.7 (10H), 1.7 (10H), 3.2 to 3.8 (73H).
$^{19}$F-NMR (282.7 MHz, solvent: CDCl$_3$, standard: CFCl$_3$) δ (ppm): −52.4 to −55.7 (42F), −77.2 (1F), −79.4 (1F), −82.2 (3F), −89.4 to −91.1 (90F), −130.5 (2F).
Average m21: 21, average m22: 20, and the number average molecular weight: 5,250.

NMR spectrum of compound (1-1b)
$^1$H-NMR (300.4 MHz, solvent: CDCl$_3$, standard: TMS) δ (ppm): 0.7 (10H), 1.7 (10H), 3.2 to 3.8 (73H), 4.2 (2H), 5.8 to 6.0 (1H).
$^{19}$F-NMR (282.7 MHz, solvent: CDCl$_3$, standard: CFCl$_3$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).
Average m21: 21, average m22: 20, and the number average molecular weight: 5,200.

NMR spectrum of compound (1-1c)
$^1$H-NMR (300.4 MHz, solvent: CDCl$_3$, standard: TMS) δ (ppm): 0.7 (10H), 1.7 (10H), 3.2 to 4.0 (73H).
$^{19}$F-NMR (282.7 MHz, solvent: CDCl$_3$, standard: CFCl$_3$) δ (ppm): −55.1 (3F), −82.6 (54F), −87.9 (54F), −90.0 (2F), −119.3 (2F), −125.0 (52F), −126.1 (2F). Average m25: 13, and the number average molecular weight: 5,750.

NMR spectrum of compound (1-3a)
$^1$H-NMR (300.4 MHz, solvent: CDCl$_3$, standard: TMS) δ (ppm): 0.7 (10H), 1.3 to 1.8 (30H), 3.2 to 3.9 (73H).
$^{19}$F-NMR (282.7 MHz, solvent: CDCl$_3$, standard: CFCl$_3$) δ (ppm): −52.4 to −55.7 (42F), −77.2 (1F), −79.4 (1F), −82.2 (3F), −89.4 to −91.1 (90F), −130.5 (2F).
Average m21: 21, average m22: 20, and the number average molecular weight: 5,390.

NMR spectrum of compound (1-3b)
$^1$H-NMR (300.4 MHz, solvent: CDCl$_3$, standard: TMS) δ (ppm): 0.7 (10H), 1.3 to 1.8 (30H), 3.2 to 3.9 (73H), 4.2 (2H), 5.8 to 6.0 (1H).
$^{19}$F-NMR (282.7 MHz, solvent: CDCl$_3$, standard: CFCl$_3$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

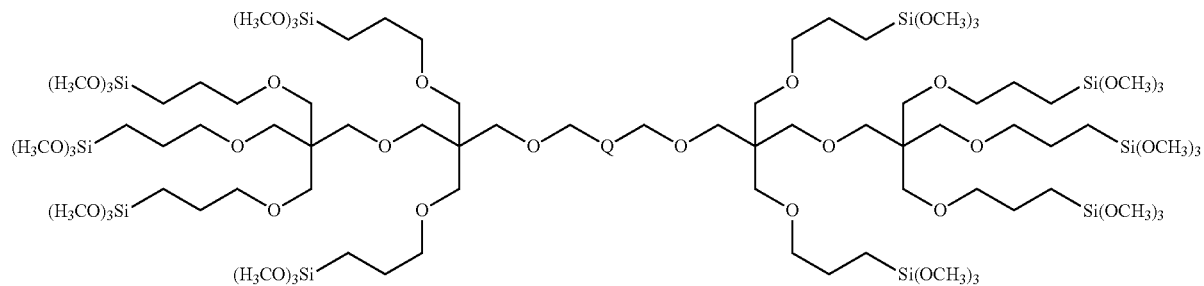

(11-1)

(R$^f$-1) to (R$^f$-3) in the table are previously shown.
Q and (R$^f$-4) in the table are represented by the following formulae.

—CF$_2$O{(CF$_2$O)$_{m21}$(CF$_2$CF$_2$O)$_{m22}$}CF$_2$— (Q)

CF$_3$CF$_2$CF$_2$O(CF(CF$_3$)CF$_2$O)$_{m26}$CF(CF$_3$)— (R$^f$-4)

Average m21: 21, average m22: 20, and the number average molecular weight: 5,340.

NMR spectrum of compound (1-3c)
$^1$H-NMR (300.4 MHz, solvent: CDCl$_3$, standard: TMS) δ (ppm): 0.7 (10H), 1.3 to 1.8 (30H), 3.2 to 4.0 (73H).

$^{19}$F-NMR (282.7 MHz, solvent: CDCl$_3$, standard: CFCl$_3$) δ (ppm): −55.1 (3F), −82.6 (54F), −87.9 (54F), −90.0 (2F), −119.3 (2F), −125.0 (52F), −126.1 (2F).

Average m25: 13, and the number average molecular weight: 5,890.

NMR spectrum of compound (1-4a)

$^1$H-NMR (300.4 MHz, solvent: CDCl$_3$, standard: TMS) δ (ppm): 0.7 (8H), 1.3 to 1.8 (24H), 3.2 to 3.9 (64H).

$^{19}$F-NMR (282.7 MHz, solvent: CDCl$_3$, standard: CFCl$_3$) δ (ppm): −52.4 to −55.7 (84F), −77.2 (2F), −79.4 (2F), −82.2 (6F), −89.4 to −91.1 (180F), −130.5 (4F).

Average m21: 21, average m22:20, and the number average molecular weight: 9,390.

NMR spectrum of compound (1-4b)

$^1$H-NMR (300.4 MHz, solvent: CDCl$_3$, standard: TMS) δ (ppm): 0.7 (8H), 1.3 to 1.8 (24H), 3.2 to 3.9 (64H), 4.2 (4H), 5.8 to 6.0 (2H).

$^{19}$F-NMR (282.7 MHz, solvent: CDCl$_3$, standard: CFCl$_3$) δ (ppm): −51.2 to −54.6 (84F), −77.2 (2F), −77.7 (2F), −79.3 (2F), −79.7 (2F), −81.2 (6F), −84.3 to −87.2 (4F), −87.9 to −91.0 (164F), −129.4 (4F), −144.1 (2F).

Average m21:21, average m22:20, and the number average molecular weight: 9,280.

NMR spectrum of compound (1-4c)

$^1$H-NMR (300.4 MHz, solvent: CDCl$_3$, standard: TMS) δ (ppm): 0.7 (8H), 1.3 to 1.8 (24H), 3.2 to 4.0 (64H).

$^{19}$F-NMR (282.7 MHz, solvent: CDCl$_3$, standard: CFCl$_3$) δ (ppm): −55.1 (6F), −82.6 (108F), −87.9 (108F), −90.0 (4F), −119.3 (4F), −125.0 (104F), −126.1 (4F).

Average m25: 13, and the number average molecular weight: 10,380.

NMR spectrum of compound (1-5a)

$^1$H-NMR (300.4 MHz, solvent: CDCl$_3$, standard: TMS) δ (ppm): 0.7 (4H), 1.3 to 1.8 (12H), 3.2 to 3.9 (34H).

$^{19}$F-NMR (282.7 MHz, solvent: CDCl$_3$, standard: CFCl$_3$) δ (ppm): −52.4 to −55.7 (84F), −77.2 (2F), −79.4 (2F), −82.2 (6F), −89.4 to −91.1 (180F), −130.5 (4F).

Average m21: 21, average m22: 20, and the number average molecular weight: 8,890.

NMR spectrum of compound (1-5c)

$^1$H-NMR (300.4 MHz, solvent: CDCl$_3$, standard: TMS) δ (ppm): 0.7 (4H), 1.3 to 1.8 (12H), 3.2 to 4.0 (34H).

$^{19}$F-NMR (282.7 MHz, solvent: CDCl$_3$, standard: CFCl$_3$) δ (ppm): −55.1 (6F), −82.6 (108F), −87.9 (108F), −90.0 (4F), −119.3 (4F), −125.0 (104F), −126.1 (4F).

Average m25: 13, and the number average molecular weight: 9,880.

NMR spectrum of compound (1-6a)

$^1$H-NMR (300.4 MHz, solvent: CDCl$_3$, standard: TMS) δ (ppm): 0.7 (2H), 0.9 (3H), 1.3 to 1.8 (8H), 3.2 to 3.9 (21H).

$^{19}$F-NMR (282.7 MHz, solvent: CDCl$_3$, standard: CFCl$_3$) δ (ppm): −52.4 to −55.7 (84F), −77.2 (2F), −79.4 (2F), −82.2 (6F), −89.4 to −91.1 (180F), −130.5 (4F).

Average m21: 21, average m22: 20, and the number average molecular weight: 8,700.

NMR spectrum of compound (1-6c)

$^1$H-NMR (300.4 MHz, solvent: CDCl$_3$, standard: TMS) δ (ppm): 0.7 (2H), 0.9 (3H), 1.3 to 1.8 (8H), 3.2 to 4.0 (21H).

$^{19}$F-NMR (282.7 MHz, solvent: CDCl$_3$, standard: CFCl$_3$) δ (ppm): −55.1 (6F), −82.6 (108F), −87.9 (108F), −90.0 (4F), −119.3 (4F), −125.0 (104F), −126.1 (4F).

Average m25: 13, and the number average molecular weight: 9,680.

NMR spectrum of compound (11-1)

$^1$H-NMR (300.4 MHz, solvent: CDCl$_3$, standard: TMS) δ (ppm): 0.7 (20H), 1.7 (20H), 3.2 to 3.8 (146H).

$^{19}$F-NMR (282.7 MHz, solvent: CDCl$_3$, standard: CFCl$_3$) δ (ppm): −52.4 to −55.7 (42F), −77.2 (2F), −79.4 (2F), −89.4 to −91.1 (80F).

Average m21: 21, average m22: 20, and the number average molecular weight: 5,960.

NMR spectrum of compound (11-2)

$^1$H-NMR (300.4 MHz, solvent: CDCl$_3$, standard: TMS) δ (ppm): 0.7 (10H), 1.7 (10H), 3.2 to 3.8 (71H).

$^{19}$F-NMR (282.7 MHz, solvent: CDCl$_3$, standard: CFCl$_3$) δ (ppm): −78.4 to −82.2 (38F), −129.4 (2F), −131.1 (1F), −144.2 (6F).

Average m26: 6, and the number average molecular weight: 2,360.

Ex. 16

Production of Compound (1-7) Having R$^f$ Represented by the Formula (R$^f$-3) (Compound (1-7c))

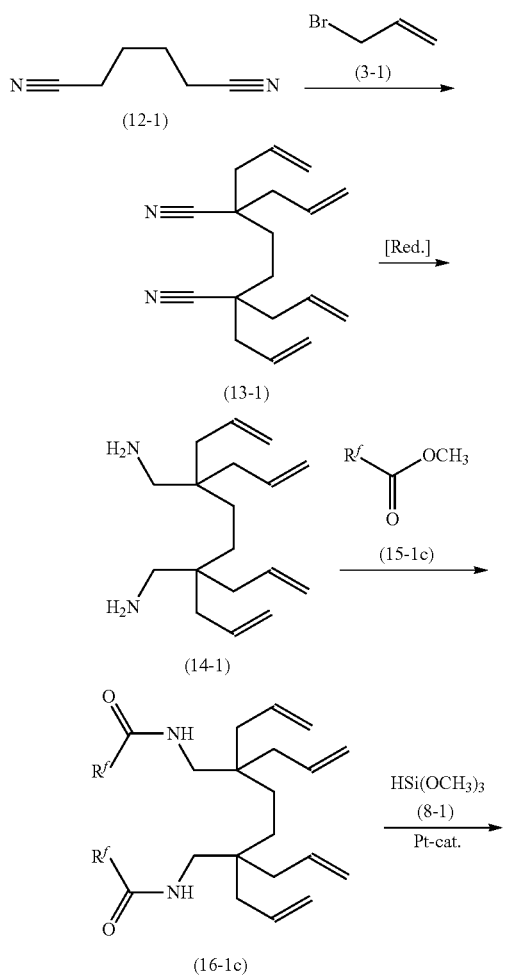

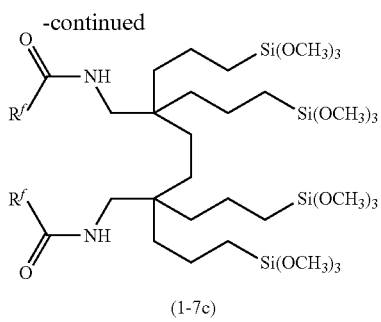

(1-7c)

In a 200 mL three-necked flask, 0.94 g of compound (12-1) and 35.1 g of tetrahydrofuran (hereinafter referred to also as THF) were stirred with cooling to −70° C. 7.5 mL of 1.13 mol/L hexane solution of isopropylaminolithium was gradually added, and then gradual addition of 1.20 g of compound (3-1) and 1 hour of stirring were repeated four times, followed by another 1 hour of stirring at room temperature. After addition of 1.0 g of water, the crude reaction solution was concentrated in an evaporator, and, after addition of 30 g of cyclopentyl methyl ether, washed with water three times, and the organic layer was recovered. The recovered solution was concentrated in an evaporator to obtain 2.05 g of a crude product. The crude product was separated by silica gel column chromatography to obtain 1.22 g of compound (13-1) (yield 53%).

NMR spectrum of compound (13-1)
$^1$H-NMR (300.4 MHz, solvent: CDCl$_3$, standard: TMS) δ (ppm): 1.7 (4H), 2.3 (8H), 5.2 (8H), 5.8 (4H).

In a 100 mL three-necked recovery flask, 4.5 mL of 2.5 mol/L THF solution of lithium aluminum hydride and 30 mL of THF were stirred at 0° C. A solution of 1.00 g of compound (13-1) in 4 mL of THF was gradually added, and the reaction solution was stirred for 1 hour and then stirred at room temperature for another 12 hours. The crude reaction solution was quenched with 1.03 g of sodium sulfate decahydrate, and after separation of the solid by filtration, concentrated in an evaporator to obtain 0.75 g of a crude product. The crude product was separated by silica gel chromatography to obtain 0.39 g of compound (14-1) (yield 38%).

NMR spectrum of compound (14-1)
$^1$H-NMR (300.4 MHz, solvent: CDCl$_3$, standard: TMS) δ (ppm): 1.1 (4H), 1.2 (4H), 2.0 (4H), 2.5 (8H), 5.0 (8H), 5.8 (4H).

In a 30 mL recovery flask, 12.6 g of compound (15-1c) and 0.30 g of compound (14-1) were stirred at room temperature for 12 hours to obtain a crude reaction solution. The crude reaction solution was separated by silica gel chromatography to obtain 4.50 g of compound (16-1c) (yield 43%).

NMR spectrum of compound (16-1c)
$^1$H-NMR (300.4 MHz, solvent: CDCl$_3$, standard: TMS) δ (ppm): 1.4 (4H), 2.1 (8H), 3.3 (4H), 5.1 (8H), 5.9 (4H).
$^{19}$F-NMR (282.7 MHz, solvent: CDCl$_3$, standard: CFCl$_3$) δ (ppm): −55.3 (6F), −82.8 (108F), −88.1 (108F), −90.2 (4F), −119.3 (4F), −125.3 (108F).

Average m25: 13, and the number average molecular weight: 9,660.

In a 9 mL polypropylene vessel, 2.0 g of compound (16-1c), 6.7 mg of a xylene solution of platinum/1,3-divinyl-1,1,3,3-tetramethyldisiloxane complex (platinum content: 3%), 0.14 g of compound (8-1), 0.6 mg of aniline and 2.0 g of C$_6$F$_{13}$C$_2$H$_5$ (ASAHIKLIN (registered trademark) AC-6000, manufactured by Asahi Glass Company, Limited) were stirred at 40° C. for 4 hours. The solvent was distilled off under reduced pressure, and the residue was filtered through a membrane filter having a pore size of 0.2 μm to obtain 2.0 g of compound (1-7c) derived from compound (16-1c) by hydrosilylation of the 5 ally groups in compound (16-1c). The hydrosilylation proceeded with a 100% conversion and with a 100% selectivity for hydrosilylation.

NMR spectrum of compound (1-7c)
$^1$H-NMR (300.4 MHz, solvent: CDCl$_3$, standard: tetramethylsilane (TMS)) δ (ppm): 0.7 (8H), 1.3 to 1.4 (12H), 1.6 (8H), 3.3 (4H), 3.7 (36H).
$^{19}$F-NMR (282.7 MHz, solvent: CDCl$_3$, standard: CFCl$_3$) δ (ppm): −55.2 (6F), −82.8 (108F), −88.0 (108F), −90.2 (4F), −118.8 (4F), −125.2 (108F).

Average m25: 13, and the number average molecular weight: 10,100.

Ex. 17

Production of Compound) 1-8) Having R$^f$ Represented by the Formula (R$^f$-3) (Compound (1-8c))

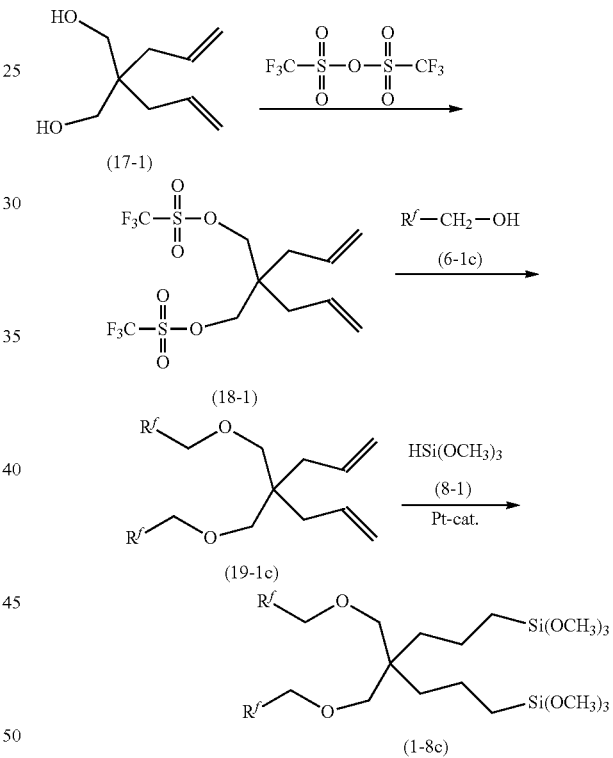

In a 50 mL two-necked recovery flask, 2.0 g of compound (17-1), 4.1 g of 2,6-lutidine and 6.0 g of AE-3000 were stirred with cooling on an ice bath, while 10.8 g of trifluoromethanesulfonic anhydride was gradually added dropwise under a nitrogen atmosphere. After another 1 hour of stirring, the reaction solution was washed with dilute aqueous hydrochloric acid, and the organic phase was recovered. The recovered organic phase was concentrated in an evaporator to obtain a crude product. The crude product was separated by silica gel chromatography to obtain 5.1 g of compound (18-1) (yield 94%).

NMR spectrum of compound (18-1)
$^1$H-NMR (300.4 MHz, solvent: CDCl$_3$, standard: tetramethylsilane (TMS)) δ (ppm): 2.1 (4H), 4.3 (4H), 5.3 (4H), 5.7 (2H).

$^{19}$F-NMR (282.7 MHz, solvent: CDCl$_3$, standard: CFCl$_3$) δ (ppm): −74.0 (6F).

In a 50 mL recovery flask, 0.20 g of compound (18-1), 4.47 g of compound (6-1c), 1.24 g of cesium carbonate and 5.9 g of AC-6000 were stirred at 80° C. from 12 hours under reflux. After addition of 10 g of AC-6000, the reaction solution was washed with dilute aqueous hydrochloric acid once, and the organic phase was recovered. The recovered solution was concentrated in an evaporator to obtain a crude product. The crude product was separated by silica gel chromatography to obtain 3.5 g of compound (19-1c) (yield 77%).

NMR spectrum of compound (19-1c)
$^1$H-NMR (300.4 MHz, solvent: CDCl$_3$, standard: tetramethylsilane (TMS)) δ (ppm): 2.0 (4H), 3.4 (4H), 3.9 (4H), 5.1 (4H), 5.8 (2H).
$^{19}$F-NMR (282.7 MHz, solvent: CDCl$_3$, standard: CFCl$_3$) δ (ppm): −55.2 (6F), −82.7 (108F), −88.0 (108F), −90.1 (4F), −119.4 (4F), −125.1 (104F), −126.2 (4F).

Average m25:13, and the number average molecular weight: 9,520.

In a 9 mL polypropylene vessel, 2.0 g of compound (19-1c), 6.5 mg of a xylene solution of platinum/1,3-divinyl-1,1,3,3-tetramethyldisiloxane complex (platinum content: 3%), 0.07 g of compound (8-1), 0.6 mg of aniline and 2.0 g of AC-6000 were stirred at 40° C. for 4 hours. The solvent was distilled off under reduced pressure, and the residue was filtered through a membrane filter having a pore size of 0.2 µm to obtain 2.0 g of compound (1-8c) resulting from hydrosilylation of the two allyl groups in compound (19-1c). The hydrosilylation proceeded with a 100% conversion and a 100% selectivity for hydrosilylation.

NMR spectrum of compound (1-8c)
$^1$H-NMR (300.4 MHz, solvent: CDCl$_3$, standard: tetramethylsilane (TMS)) δ (ppm): 2.0 (4H), 3.4 (4H), 3.9 (4H), 5.1 (4H), 5.8 (2H). 0.7 (4H), 1.5 to 1.7 (8H), 3.4 to 3.8 (26H).
$^{19}$F-NMR (282.7 MHz, solvent: CDCl$_3$, standard: CFCl$_3$) δ (ppm): −55.2 (6F), −82.7 (108F), −88.0 (108F), −90.1 (4F), −119.4 (4F), −125.1 (104F), −126.2 (4F).

Average m25: 13, and the number average molecular weight: 9,760.

Ex. 18 to Ex. 34

Surface treatment of substrates was carried out with compounds and compositions obtained in Ex. 1 to Ex. 17 to give articles of Ex. 18 to Ex. 34. As the surface treatment method, the following dry coating and wet coating methods were, respectively, used for each Ex. As the substrates, chemically tempered glass was used. The resulting articles were evaluated by the following methods. The results are shown in Tables 2 to 5.

(Dry Coating Method)

The dry coating was conducted by means of a vacuum vapor deposition apparatus (SGC-22WA, manufactured by SHOWA SHINKU CO., LTD.) (vacuum vapor deposition). 0.35 mg of a compound or composition obtained in each Ex. was charged into a molybdenum boat in the vacuum vapor deposition apparatus, and the inside of the vacuum vapor deposition apparatus was evacuated to 1×10$^{-3}$ Pa or below. Each compound or composition was deposited on a substrate by heating the boat loading the compound or composition to form a deposited film on the surface of the substrate. The substrate having the deposited film was incubated at a temperature of 25° C. at a humidity of 50% to obtain an article having a surface layer on the substrate.

(Wet Coating Method)

A compound or composition obtained in each Ex. and AC-6000 as a liquid medium were mixed to prepare a coating liquid having a solid content of 0.1%. The coating liquid was sprayed onto a substrate by means of a spray coater (manufactured by Nordson Corporation) to form a coating film on the substrate. The substrate having a coating film was baked at 120° C. for 20 minutes to obtain an article having a surface layer on the substrate.

(Evaluation Methods)
<Method for Measuring Contact Angle>

A contact angle of about 2 µL of distilled water or n-hexadecane with a surface layer was measured with a contact angle meter DM-500 (manufactured by Kyowa Interface Science Co., Ltd.). Measurements are made at five different locations on the surface of the surface layer and averaged. For the calculation of the contact angle, the 2θ method was used.

<Initial Contact Angle>

With respect to a substrate having a surface-treated layer, the initial contact angles of water and n-hexadecane with a surface layer were measured by the above measuring method and rated on the following scale.

Initial water contact angle:
⊚ (excellent): at least 115°
○ (good): at least 110° and less than 115°
Δ (fair): at least 100° and less than 110°
× (bad): less than 100°
Initial n-hexadecane contact angle
⊚ (excellent): at least 66°
○ (good): at least 65° and less than 66°
Δ (fair): at least 63° and less than 65°
× (bad): less than 63°

<Abrasion Resistance (Against Steel Wool)>

A surface layer was rubbed with steel wool Bon Star (#0000) reciprocating at a speed of 320 cm/min 5000 times under a pressure of 98.07 kPa using a reciprocating traverse tester (manufactured by KNT Co., Ltd.) in accordance with JIS L0849:2013 (ISO 105-X12: 2001), and then the water contact angle was measured. If the decrease in water repellency (water contact angle) observed after the rubs is small, the surface layer is excellent in abrasion resistance with little damage to its performance by the rubs. The scale for evaluations is given below.

⊚ (excellent): The water contact angle had changed by at most 5° after 5000 reciprocating rubs.
○ (good): The water contact angle had changed by at least 5° and less than 10° after 5000 reciprocating rubs.
Δ (fair): The water contact angle had changed by at least 10° and less than 20° after 5000 reciprocating rubs.
× (bad): The water contact angle had changed by at least 20° after 5000 reciprocating rubs.

<Abrasion Resistance (Against Eraser)>

A surface layer was rubbed with Rubber Eraser (manufactured by Minoan) reciprocating at a speed of 60 rpm 10,000 times under a lead of 4.9 N using a reciprocating traverse tester (manufactured by KNT Co., Ltd.) in accordance with JIS L0849:2013 (ISO 105-X12: 2001), and then the water contact angle was measure. If the decrease in water repellency (water contact angle) observed after the rubs is small, the surface layer is excellent in abrasion resistance with little damage to its performance by the rubs. The scale for evaluations is given below.

⊚ (excellent): The water contact angle had changed by at most 5° after 10,000 reciprocating rubs.
○ (good): The water contact angle had changed by at least 5° and less than 10° after 10,000 reciprocating rubs.

Δ (fair): The water contact angle had changed by at least 10° and less than 20° after 10,000 reciprocating rubs.

× (bad): The water contact angle had changed by at least 20° after 10,000 reciprocating rubs.

<Appearance>

The haze of an article was measured with a haze meter (manufactured by Toyo Seiki Seisaku-sho, Ltd.). A small haze means that the article has an even coating of a fluorinated ether compound and is excellent in appearance.

⊚ (excellent): The haze was at most 0.1%.
○ (good): The haze was higher than 0.1% and at most 0.2%.
Δ (fair): The haze was higher than 0.2% and at most 0.3%.
× (bad): The haze was higher than 0.3%.

<Fingerprint Stain Removability>

An artificial fingerprint liquid (liquid consisting of oleic acid and squalene) was put on a flat surface of a silicone rubber stopper, and then, excess oil was wiped off by a nonwoven fabric (BEMCOT M-3, manufactured by Asahi Kasei Corporation), to prepare a fingerprint stamp. The fingerprint stamp was placed on a surface layer and pressed under a load of 9.8 N for 10 seconds. The haze at a portion stained with the fingerprint was measured by a haze meter (manufactured by Toyo Seiki Seisaku-Sho, Ltd.) and was taken as the initial value. Then, the portion of the surface layer stained with the fingerprint was wiped with tissue paper under a load of 500 g by means of a reciprocating traverse tester (manufactured by KNT Co., Ltd.). The haze was measured every single reciprocating wipe to determine the number of reciprocating rubs required to lower the haze from the initial value to 10% or below. A surface layer which requires few wipes is easy to remove a fingerprint stain from and is excellent in fingerprint removability. The scale for evaluations is given below.

⊚ (excellent): The number of required wipes was at most 3.
○ (good): The number of required wipes was from 4 to 5.
Δ (fair): The number of required wipes was from 6 to 8.
× (bad): The number of required wipes was from at least 9.

<Light Resistance>

A surface layer was irradiated with light rays (650 W/m$^2$, 300 to 700 nm) for 500 hours at a black panel temperature of 63° C. for 500 hours by means of a desk-top xenon arc lamp light fastness tester for accelerated tests equipped with a xenon lamp (SUNTEST XLS+, manufactured by Toyo Seiki Seisaku-sho, Ltd.), and then the water contact angle was measured. If the decrease in water contact angle observed after the accelerated light fastness test is small, the surface layer is excellent in light resistance with little damage to its performance by the light. The scale for evaluations is given below.

⊚ (excellent): The water contact angle had changed by at most 5° after the accelerated light fastness test.
○ (good): The water contact angle had changed by at least 5° and less than 10° after the accelerated light fastness test.
Δ (fair): The water contact angle had changed by at least 10° and less than 20° after the accelerated light fastness test.
× (bad): The water contact angle had changed by at least 20° after the accelerated light fastness test.

<Lubricity>

The kinetic coefficient of friction between a surface layer and an artificial skin (PBZ13001, manufactured by Idemitsu Technofine Co., Ltd.) was measured over a contact area of 3 cm×3 cm under a load of 0.98 N. A surface layer having a smaller kinetic coefficient of friction is excellent in lubricity. The scale for evaluations is given below.

⊚ (excellent): The kinetic coefficient of friction was at most 0.3.
○ (good): The kinetic coefficient of friction was larger than 0.3 and at most 0.4.
Δ (fair): The kinetic coefficient of friction was larger than 0.4 and at most 0.5.
× (bad): The kinetic coefficient of friction was larger than 0.5.

TABLE 2

| | | Ex. | | | | |
| --- | --- | --- | --- | --- | --- | --- |
| | | 18 | 19 | 20 | 21 | 22 |
| Fluorinated ether compound/composition | kind | Composition (A): compound (1-1a) + by-products | Composition (B): compound (1-1b) + by-products | Composition (C): compound (1-1c) + by-products | Compound (1-3a) | Compound (1-3a) |
| | Conversion in hydrosilylation (%) | 100 | 100 | 100 | 100 | 100 |
| | Selectivity for hydrosilylation (%) | 82 | 82 | 81 | 100 | 100 |
| Dry coating | Initial contact angle  Water | ○ | ○ | ○ | ○ | ○ |
| | n-Hexadecane | ○ | ○ | ○ | ○ | ○ |
| | Abrasion resistance (steel wool) | Δ | Δ | ○ | ○ | ○ |
| | Abrasion resistance (eraser) | ○ | Δ | Δ | ○ | Δ |
| Wet coating | Initial contact angle  Water | ○ | ○ | ○ | ○ | ○ |
| | n-Hexadecane | ○ | ○ | ○ | ○ | ○ |
| | Abrasion resistance (steel wool) | Δ | Δ | Δ | Δ | Δ |
| | Abrasion resistance (eraser) | Δ | Δ | Δ | ○ | Δ |
| | Appearance | ○ | ⊚ | ○ | ⊚ | ⊚ |
| | Fingerprint stain removability | ⊚ | ⊚ | ⊚ | ⊚ | ⊚ |
| | Light resistance | ○ | ○ | ○ | ○ | ○ |
| | Lubricity | ⊚ | ⊚ | ○ | ⊚ | ⊚ |

TABLE 3

|  |  | Ex. 23 | Ex. 24 | Ex. 25 | Ex. 26 | Ex. 27 |
|---|---|---|---|---|---|---|
| Fluorinated ether compound/ composition | kind | Compound (1-3c) | Compound (1-4c) | Compound (1-4b) | Compound (1-4c) | Compound (1-5c) |
|  | Conversion in hydrosilylation (%) | 100 | 100 | 100 | 100 | 100 |
|  | Selectivity for hydrosilylation (%) | 100 | 100 | 100 | 100 | 100 |
| Dry coating | Initial contact angle  Water | △ | ○ | △ | ○ | ○ |
|  | n-Hexadecane | ○ | ◎ | ○ | ◎ | ◎ |
|  | Abrasion resistance (steel wool) | △ | ○ | ○ | ◎ | ○ |
|  | Abrasion resistance (eraser) | ◎ | ○ | △ | ◎ | ○ |
| Wet coating | Initial contact angle  Water | △ | ○ | △ | ○ | ◎ |
|  | n-Hexadecane | ○ | ◎ | ○ | ◎ | ◎ |
|  | Abrasion resistance (steel wool) | △ | ○ | ○ | ◎ | △ |
|  | Abrasion resistance (eraser) | ○ | ○ | △ | ◎ | ○ |
|  | Appearance | ◎ | ◎ | ◎ | △ | ○ |
|  | Fingerprint stain removability | ◎ | ◎ | ◎ | ◎ | ◎ |
|  | Light resistance | ○ | ○ | ○ | ○ | △ |
|  | Lubricity | ○ | ◎ | ◎ | ○ | ◎ |

TABLE 4

|  |  | Ex. 28 | Ex. 29 | Ex. 30 | Ex. 31 | Ex. 32 |
|---|---|---|---|---|---|---|
| Fluorinated ether compound/ composition | kind | Compound (1-5c) | Compound (1-6c) | Compound (1-6c) | Composition (D): compound (11-1) + by-products | Composition (E): compound (11-2) + by-products |
|  | Conversion in hydrosilylation (%) | 100 | 100 | 100 | 100 | 100 |
|  | Selectivity for hydrosilylation (%) | 100 | 100 | 100 | 82 | 80 |
| Dry coating | Initial contact angle  Water | ◎ | ○ | ○ | △ | ○ |
|  | n-Hexadecane | ◎ | ◎ | ◎ | △ | ○ |
|  | Abrasion resistance (steel wool) | ○ | △ | △ | △ | X |
|  | Abrasion resistance (eraser) | ○ | △ | △ | △ | X |
| Wet coating | Initial contact angle  Water | ◎ | ○ | ○ | △ | ○ |
|  | n-Hexadecane | ◎ | ◎ | ◎ | △ | ○ |
|  | Abrasion resistance (steel wool) | ○ | △ | △ | X | X |
|  | Abrasion resistance (eraser) | ○ | △ | △ | △ | X |
|  | Appearance | ◎ | ○ | △ | X | ◎ |
|  | Fingerprint stain removability | ◎ | ◎ | ◎ | X | ○ |
|  | Light resistance | △ | △ | △ | △ | X |
|  | Lubricity | ○ | ◎ | ○ | △ | X |

TABLE 5

|  |  | Ex. 33 | Ex. 34 |
|---|---|---|---|
| Fluorinated ether compound/ composition | kind | Compound (1-7c) | Compound (1-8c) |
|  | Conversion in hydrosilylation (%) | 100 | 100 |
|  | Selectivity for hydrosilylation (%) | 100 | 100 |
| Dry coating | Initial contact angle  Water | ◎ | ◎ |
|  | n-Hexadecane | ◎ | ◎ |
|  | Abrasion resistance (steel wool) | ◎ | ○ |
|  | Abrasion resistance (eraser) | ○ | ○ |
| Wet coating | Initial contact angle  Water | ◎ | ◎ |
|  | n-Hexadecane | ◎ | ◎ |
|  | Abrasion resistance (steel wool) | ◎ | ○ |
|  | Abrasion resistance (eraser) | ○ | ○ |
|  | Appearance | ○ | ○ |
|  | Fingerprint stain removability | ◎ | ◎ |
|  | Light resistance | ◎ | ○ |
|  | Lubricity | ○ | ○ |

When compound (1) or a composition containing compound (1) was used in Ex. 18 to Ex. 30 and Ex. 33 to Ex. 34, the water/oil repellency, abrasion resistance, appearance, fingerprint stain removability, light resistance and lubricity were excellent.

When a composition containing compound (11-1) having hydrolyzable silyl groups at both ends was used in Ex. 31, the abrasion resistance, appearance, fingerprint stain removability and light resistance were poor. It seems that the poor fingerprint stain removability resulted from the surface physical properties impaired by the unreacted terminal groups. It seems that the poor appearance and abrasion resistance resulted from poor uniformity due to agglomeration of non-fluorinated terminals. The abrasion resistance was poor probably because both terminals were fixed to the substrate.

When a composition containing compound (11-2) having a branched poly(oxyperfluoroalkylene) chain in Ex. 32, the abrasion resistance deteriorated greatly probably because hindrance to the molecular motility by the branched structure led to a huge drop in lubricity.

INDUSTRIAL APPLICABILITY

The fluorinated ether compound of the present invention is useful for surface treatment to impart water/oil repellency to a surface of a substrate such as a member of optical products, touch panels (surfaces to be touched by a finger), anti-reflection film, anti-reflection glass, $SiO_2$-treated glass, tempered glass, sapphire glass, quartz substrate and metal molds. It is also useful as a release agent (for metal molds and the like).

This application is a continuation of PCT Application No. PCT/JP2017/007897, filed on Feb. 28, 2017, which is based upon and claims the benefit of priority from Japanese Patent Application No. 2014-087043 filed on Apr. 25, 2016 and Japanese Patent Application No. 2016-159202 filed on Aug. 15, 2016. The contents of those applications are incorporated herein by reference in their entireties.

What is claimed is:

1. A fluorinated ether compound represented by the following formula (1):

$$[R^f\text{-}G\text{-}]_a Z[\text{---}(O\text{---}R^2)_c\text{---}SiR^3{}_n L_{3-n}]_b \quad (1)$$

wherein $R^f$ is a linear polyfluoroalkyl group having at least two carbon atoms, which has at least one etheric oxygen between carbon-carbon atoms and has at least one fluorine atoms on a carbon atom bonded to G or Z, G is $-R^1-O-$, $-R^1-CONH-$, $-CONH-$ or a single bond, $R^1$ is an alkylene group, Z is a hydrocarbon group having a valence of (a+b) or a hydrocarbon group having at least two carbon atoms, having at least one etheric oxygen atom between carbon-carbon atoms and having a valence of (a+b), $R^2$ is an alkylene group, $R^3$ is a hydrogen atom or a monovalent hydrocarbon group, L is a hydrolyzable group, n is an integer of from 0 to 2, a is an integer of at least 1, b is an integer of at least 1, (a+b) is at least 3, when a is 1, b is at least 4, and when a is at least 2, b is at least 1, provided that when a is at least 2, each [$R^f$-G-] may be identical with or different from one another, and when b is at least 2, each [$-(O-R^2)_c-SiR^3{}_n L_{3-n}$] may be identical with or different from one another, and c is 0 or 1.

2. The fluorinated ether compound according to claim 1, wherein c is 1 and $R^2$ is a $C_{4-14}$ alkylene group.

3. The fluorinated ether compound according to claim 1, wherein Z is a group represented by the following formula (Z-1), a group represented by the following formula (Z-2), a group represented by the following formula (Z-3), a group represented by the following formula (Z-4) or a group represented by the following formula (Z-5):

(Z-1)

(Z-2)

(Z-3)

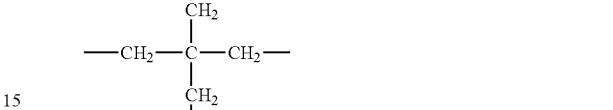

(Z-4)

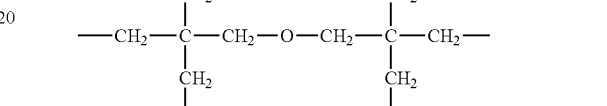

(Z-5)

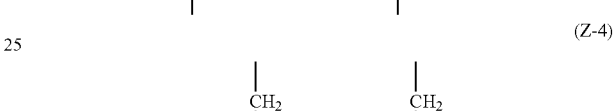

wherein $R^4$ is an alkyl group.

4. The fluorinated ether compound according to claim 1, wherein $R^1$ is $-CH_2-$.

5. The fluorinated ether compound according to claim 1, wherein $R^f$ is a group represented by the following formula ($R^f$-0):

$$R^{f1}O(R^{f2}O)_{m1}(R^{f3}O)_{m2}R^{f4}- \quad (R^f\text{-}0)$$

wherein when m1 is 0, $R^{f1}$ is a $C_{1-20}$ linear perfluoroalkyl group, and when m1 is at least 1, $R^{f1}$ is a $C_{1-20}$ linear perfluoroalkyl group or a $C_{2-20}$ linear perfluoroalkyl group having at least one etheric oxygen atom between carbon-carbon atoms, $R^{f2}$ is a $C_{1-10}$ linear fluoroalkylene group having at least one hydrogen atom, m1 is an integer of from 0 to 10, provided that when m1 is at least 2, $(R^{f2}O)_{m1}$ may be composed of at least two kinds of $R^{f2}O$ different in either or both of the number of carbon atoms and the number of hydrogen atoms, $R^{f3}$ is a $C_{1-10}$ linear perfluoroalkylene group, m2 is an integer of from 2 to 200, provided that $(R^{f3}O)_{m2}$ may be composed of at least two kinds of $R^{f3}O$ different in the number of carbon atoms, and $R^{f4}$ is a $C_{1-10}$ linear perfluoroalkylene group.

6. The fluorinated ether compound according to claim 1, wherein $R^f$ is a linear perfluoroalkyl group having at least two carbon atoms and having at least one etheric oxygen atoms between carbon-carbon atoms.

7. The fluorinated ether compound according to claim 1, wherein $R^f$ is a group represented by the following formula ($R^f$-1), a group represented by the following formula ($R^f$-2) or a group represented by the following formula ($R^f$-3):

$$R^{f1}O\{(CF_2O)_{m21}(CF_2CF_2O)_{m22}\}CF_2— \quad (R^f\text{-}1)$$

$$R^{f1}OCHFCF_2OCH_2CF_2O\{(CF_2O)_{m21}(CF_2CF_2O)_{m22}\}CF_2— \quad (R^f\text{-}2)$$

$$R^{f1}O(CF_2CF_2OCF_2CF_2CF_2CF_2O)_{m25}CF_2CF_2OCF_2CF_2CF_2— \quad (R^f\text{-}3)$$

wherein $R^{f1}$ is a $C_{1-20}$ perfluoroalkyl group,
each of m21 and m22 is an integer of at least 1, m21+m22 is an integer of from 2 to 200, provided that each $CF_2O$ and each $CF_2CF_2O$ may be bonded in any order, and m25 is an integer of from 1 to 100.

8. The fluorinated ether compound according to claim 1, which has a number average molecular weight of from 1,000 to 30,000.

9. A coating liquid comprising the fluorinated ether compound as defined in claim 1 and a liquid medium.

10. A process for producing an article having a surface layer formed from a fluorinated ether compound, which comprises treating the surface of a substrate with the coating liquid as defined in claim 9 by wet coating.

11. An article having a surface layer formed from the fluorinated ether compound as defined in claim 1.

12. A process for producing an article having a surface layer formed from the fluorinated ether compound as defined in claim 1, which comprises treating the surface of a substrate with the fluorinated ether compound by dry coating.

13. The fluorinated ether compound according to claim 1, which is represented by one of the following formulae:

[Structures (1-1) through (1-8) shown]

* * * * *